United States Patent
Sutherland et al.

(10) Patent No.: US 12,129,235 B2
(45) Date of Patent: Oct. 29, 2024

(54) TSPO BINDERS

(71) Applicants: The University Court of the University of Glasgow, Strathclyde (GB); The University Court of the University of Edinburgh, Midlothian (GB)

(72) Inventors: Andrew Sutherland, Glasgow (GB); Sally Pimlott, Glasgow (GB); Adriana Tavares, Edinburgh (GB); Christoph Lucatelli, Edinburgh (GB)

(73) Assignees: The University Court of the University of Glasgow, Glasgow (GB); The University Court of the University of Edinburgh, Edinburgh (GB)

( * ) Notice: Subject to any disclaimer, the term of this patent is extended or adjusted under 35 U.S.C. 154(b) by 67 days.

(21) Appl. No.: 17/251,712

(22) PCT Filed: Jun. 21, 2019

(86) PCT No.: PCT/EP2019/066546
§ 371 (c)(1),
(2) Date: Dec. 11, 2020

(87) PCT Pub. No.: WO2019/243616
PCT Pub. Date: Dec. 26, 2019

(65) Prior Publication Data
US 2021/0107877 A1     Apr. 15, 2021

(30) Foreign Application Priority Data
Jun. 22, 2018    (GB) .................................... 1810312

(51) Int. Cl.
*C07D 215/48* (2006.01)
*A61K 51/04* (2006.01)

(52) U.S. Cl.
CPC ............ *C07D 215/48* (2013.01); *A61K 51/04* (2013.01); *C07B 2200/05* (2013.01)

(58) Field of Classification Search
CPC .... C07D 215/48; A61K 51/04; C07B 2200/05
USPC ...................................................... 424/9.44
See application file for complete search history.

(56) References Cited

FOREIGN PATENT DOCUMENTS

WO      WO 02/26713       4/2002

OTHER PUBLICATIONS

Shah et al. Nucl. Med. Biol. 1994, 21, 573-581. (Year: 1994).*
Alam et al., (2017) "Recent Progress in the Development of TSPO PET Ligands for Neuroinflammation Imaging in Neurological Diseases", Nucl Med Mol Imaging, (51):283-296.
Bielohuby et al., (2007) "Growth Analysis of the Mouse Adrenal Gland from Weaning to Adulthood: Time- and Gender-Dependent Alterations of Cell Size and Number in the Cortical Compartment", Am J Physiol Endocrinol Metab., (293): E139-E146.
Bird et al., (2010) "Evaluation of Translocator Protein Quantification as a Tool for Characterising Macrophage Burden in Human Carotid Atherosclerosis", Atherosclerosis, 210 (2):388-391.
Blair et al., (2013) "A Novel 18F-Labelled High Affinity Agent for PET Imaging of the Translocator Protein†", Med Chem Commun, (4):1461-1466.
Calsolaro et al., (2015) A and D Poster Presentations: P4: 11 P792.
Cappelli et al., (1997) "Mapping the Peripheral Benzodiazepine Receptor Binding Site by Conformationally Restrained Derivatives of 1-(2-Chlorophenyl)-N-methyl-N-(1-methylpropyl)-3-Isoquinolinecarboxamide (PK11195)", J. Med. Chem. 40(18):2910-2921.
Charbonneau et al., (1986) "Peripheral-Type Benzodiazepine Receptors in the Living Heart Characterized by Positron Emission Tomography", Circulation, 73 (3):476-483.
Chauveau et al., (2008) "BNuclear Imaging of Neuroinflammation: A Comprehensive Review of [11C]PK11195 Challengers", Eur J Nucl Med Mol Imaging, (35): 2304-2319.
Cosenza-Nashat et al., (2009) "Expression of the Translocator Protein of 18 kDa by Microglia, Macrophages and Astrocytes Based on Immunohistochemical Localization in Abnormal Human Brain", Neuropathol Appl Neurobiol 35(3):306-328.
Dupont et al., (2017) "Translocator Protein-18 kDa (TSPO) Positron Emission Tomography (PET) Imaging and Its Clinical Impact in Neurodegenerative Diseases", International Journal of Molecular Sciences, 18(785): 37 pages.
Endres et al., (2009) "Initial Evaluation of 11C-DPA-713, a Novel TSPO PET Ligand, in Humans", Journal of Nuclear Medicine, 50(8): 1276-1282.

(Continued)

*Primary Examiner* — Michael G. Hartley
*Assistant Examiner* — Sean R Donohue
(74) *Attorney, Agent, or Firm* — Rudy J. Ng; Bozicevic, Field & Francis LLP

(57) ABSTRACT

The invention provides a compound of formula (I), and salts, solvates and radiolabelled forms thereof, together with complexes of the compound of formula (I) with TSPO, and methods for forming such complexes, and methods for detecting the compound of formula (I), such as in complex with TSPO.

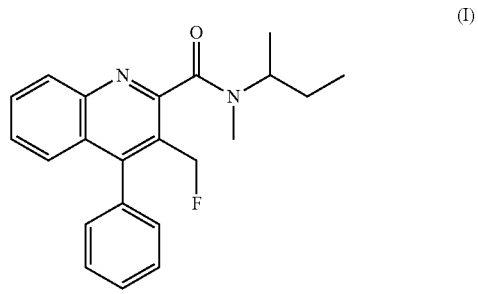

(I)

16 Claims, 13 Drawing Sheets

(56) References Cited

OTHER PUBLICATIONS

Fairweather et al. (2014) "Sex Differences in Translocator Protein 18 kDa (TSPO) in the Heart: Implications for Imaging Myocardial Inflammation", J Cardiovasc Transl Res., 7(2):192-202.
Fujimura et al., (2008) "Increased Peripheral Benzodiazepine Receptors in Arterial Plaque of Patients with Atherosclerosis: An Autoradiographic Study with [$^3$H]PK 11195", Atherosclerosis, 201:108-111.
Fujita et al., (2017) "Comparison of Four 11C-Labeled PET Ligands to Quantify Translocator Protein 18 kDa (TSPO) in Human Brain: (R)-PK11195, PBR28, DPA-713, and ER176-Based on Recent Publications that Measured Specific-to-Nondisplaceable Ratios", EJNMMI Research 7(84): 5 pages.
Gaemperli et al., (2012) "Imaging Intraplaque Inflammation in Carotid Atherosclerosis with 11C-PK11195 Positron Emission Tomography/Computed Tomography", Eur Heart J., 33:1902-1910.
Hindorf et al., (2004) "Evaluation of Parameters Influencing S Values in Mouse Dosimetry", J Nucl Med 45: 1960-1965.
Hui et al., (1994) A Mouse Model for Calculating Cross-Organ Beta Doses from Yttrium-90-Labeled Immunoconjugates, Cancer 73(3): 951-957.
Ichise et al., (2002) "Strategies to Improve Neuroreceptor Parameter Estimation by Linear Regression Analysis", J Cereb Blood Flow Metab 22:1271-1281.
Ikawa et al., (2016) "11C-ER176, a Radioligand for 18-kDa Translocator Protein, Has Adequate Sensitivity to Robustly Image All Three Affinity Genotypes in Human Brain", J Nucl Med 58(2):320-325.
Innis et al., (2007) "Consensus Nomenclature for in vivo Imaging of Reversibly Binding Radioligands", Journal of Cerebral Blood Flow & Metabolism 27:1533-1539.
Khanuja et al., (1995) "Lithl, a Major Gene Affecting Cholesterol Gallstone Formation Among Inbred Strains of Mice", PNAS 92:7729-7733.
Kobayashi et al., (2018) "11C-DPA-713 Has Much Greater Specific Binding to Translocator Protein 18 kDa (TSPO) in Human Brain than $^{11}$C-(R)-PK11195", Journal of Cerebral Blood Flow & Metabolism, 38(3):393-403.
Kreisl et al., (2010) "Comparison of [$^{11}$C]-(R)-PK 11195 and [$^{11}$C]PBR28, Two Radioligands for Translocator Protein (18 kDa) in Human and Monkey: Implications for Positron Emission Tomographic Imaging of this Inflammation Biomarker", Neuroimage 49(4):2924-2932.
Lacapere and Papadopoulos (2003) "Peripheral-Type Benzodiazepine Receptor: Structure and Function of a Cholesterol-Binding Protein in Steroid and Bile Acid Biosynthesis", Steroids 68: 569-585.
Li et al., (2015) "Crystal Structures of Translocator Protein (TSPO) and Mutant Mimic of a Human Polymorphism", Science, 347(6221):555-558.
Li et al., (2015) "Neuroprotective Effects of a Novel Translocator Protein (18 kDa) Ligand, ZBD-2, Against Focal Cerebral Ischemia and NMDA-Induced Neurotoxicity", Clin Exp Pharmacol Physio., 42:1068.
Lin et al., (1993) "The Human Peripheral Benzodiazepine Receptor Gene: Cloning and Characterization of Alternative Splicing in Normal Tissues and in a Patient with Congenital Lipoid Adrenal Hyperplasia", Genomics, 18:643-650.

Logan et al., (1996) "Distribution Volume Ratios Without Blood Sampling from Graphical Analysis of PET Data", J. Cereb Blood Flow Metab., 16(5): 834-840.
Logan (2000) "Graphical Analysis of PET Data Applied to Reversible and Irreversible Tracers", Nuclear Medicine & Biology, 27: 661-670.
Luus et al., (2010) "The Development of PET Radioligands for Imaging the Translocator Protein (18 kDa): What Have We Learned?", J. Label Compd. Radiopharm., 53:501-510.
Owen et al., (2010) "Two Binding Sites for [$^3$H]PBR28 in Human Brain: Implications for TSPO PET Imaging of Neuroinflammation", J. Cereb Blood Flow Metab., 30 1608-1618.
Owen et al., (2011) "Mixed-Affinity Binding in Humans with 18-kDa Translocator Protein Ligands", J. Nucl Med., 52(1): 24-32.
Owen et al., (2012) "An 18-kDa Translocator Protein (TSPO) Polymorphism Explains Differences in Binding Affinity of the PET Radioligand PBR28", J. Cereb Blood Flow Metab., 32: 1-5.
Papadopoulos et al., (2006) "Translocator Protein (18 kDa): New Nomenclature for the Peripheral-Type Benzodiazepine Receptor Based on its Structure and Molecular Function", Trends in Pharmacological Sciences 27(8):402-409.
Paradis et al., (2013) "Cardioprotection by the TSPO Ligand 4'-chlorodiazepam is Associated with Inhibition of Mitochondrial Accumulation of Cholesterol at Reperfusion", Cardiovasc Res., 98: 420-427.
Schaller et al., (2010) "TRO40303, a New Cardioprotective Compound, Inhibits Mitochondrial Permeability Transition", J Pharmacol Exp Ther., 333(3): 696-706.
Stabin et al., (2006) "Voxel-Based Mouse and Rat Models for Internal Dose Calculations", J Nucl Med., 47 655-659.
Thackeray et al., (2018) "Myocardial Inflammation Predicts Remodeling and Neuroinflammation After Myocardial Infarction", J Am Coll Cardiol 71(3): 263-275.
Warnock et al., (2011) "Use of a Beta Microprobe System to Measure Arterial Input Function in PET via an Arteriovenous Shunt in Rats", EJNMMI Res 1(13):11 pages.
WILMS (2003) "Involvement of Benzodiazepine Receptors in Neuroinflammatory and Neurodegenerative Diseases: Evidence from Activated Microglial Cells in vitro", Neurobio Dis., 14:417-424.
Zanotti-Fregonara et al., (2014) ACS Chem Synthesis and Evaluation of Translocator 18 kDa Protein (TSPO) Positron Emission Tomography (PET) Radioligands with Low Binding Sensitivity to Human Single Nucleotide Polymorphism rs6971, Neurosci. 5:963-971.
Anzini et al., (2001) Mapping and Fitting the Peripheral Benzodiazepine Receptor Binding Site by Carboxamide Derivatives. Comparison of Different Approaches to Quantitative Ligand-Receptor Interaction ModelingJ. Med. Chem., 44 (8):1134-1150.
Blair et al., (2015) "A Novel 18F-Labelled High Affinity Agent for PET Imaging of the Translocator Protein†", Chem. Science 6 (8):4772-4777.
Cappelli et al., (2006) "Synthesis, Labeling, and Biological Evaluation of Halogenated 2-Quinolinecarboxamides as Potential Radioligands for the Visualization of Peripheral Benzodiazepine Receptors", Bioorg. med. Chem. Letters 14 (12):4055-4066.
International Search Report and WO for PCTEP2019066546 (Aug. 6, 2019) 13 pages.
Search Report for GB 1810312.7 (Dec. 27, 2018) 5 pages.
Stevenson et al., (2010) "New Iodinated Quinoline-2-Carboxamides for SPECT Imaging of the Translocator Protein", Bioorg. Med. Chem. Letters 20 (3): 954-957.

* cited by examiner

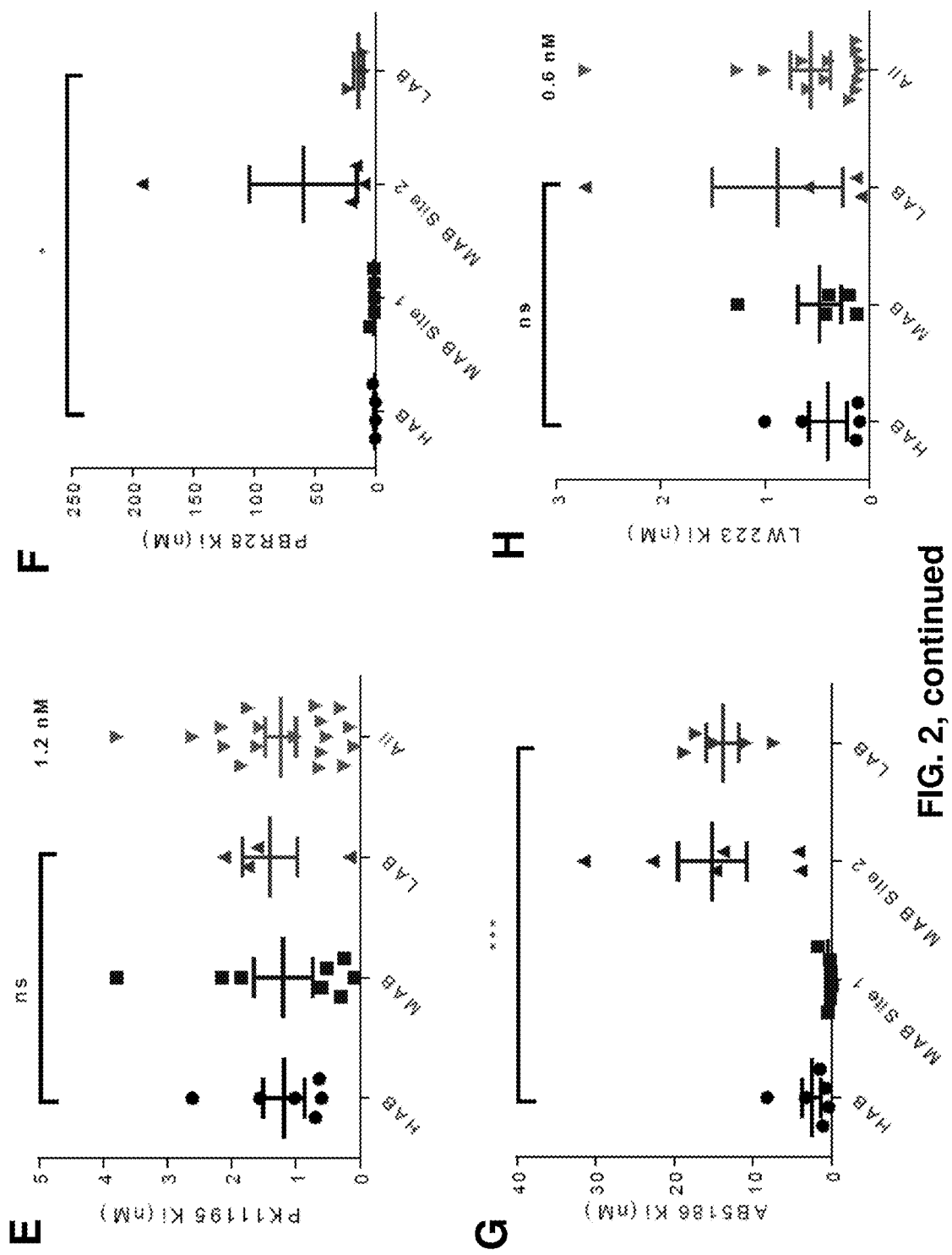
FIG. 2, continued

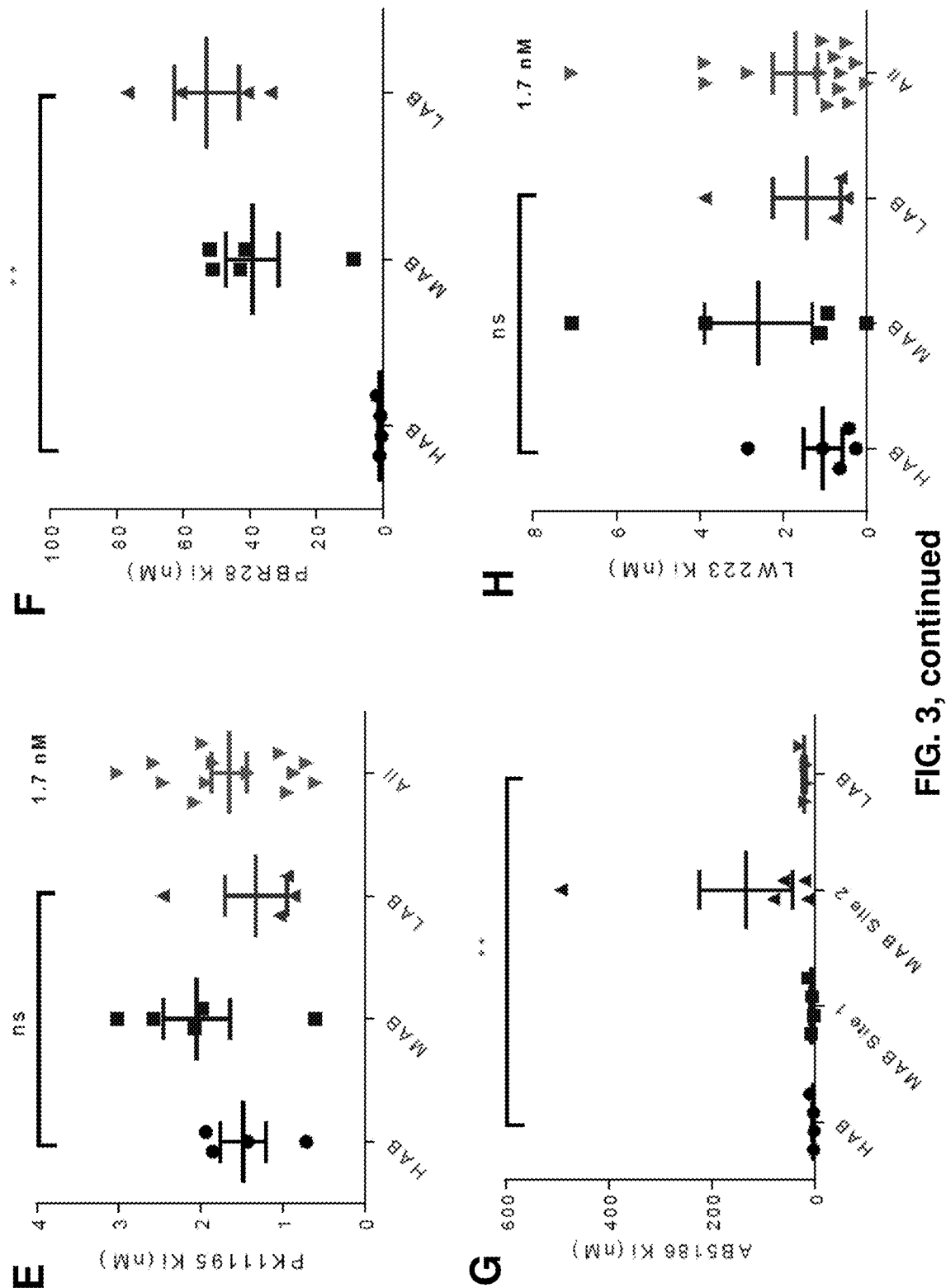
FIG. 3, continued

FIG. 11, continued
B
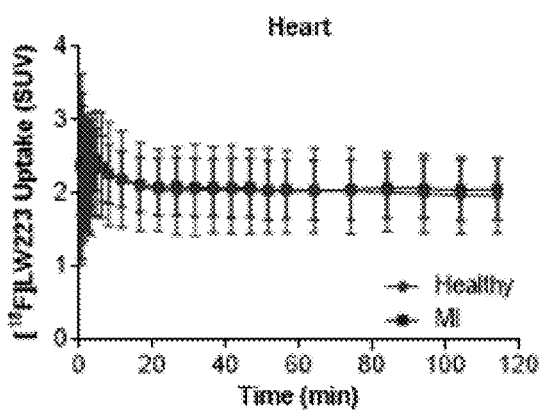
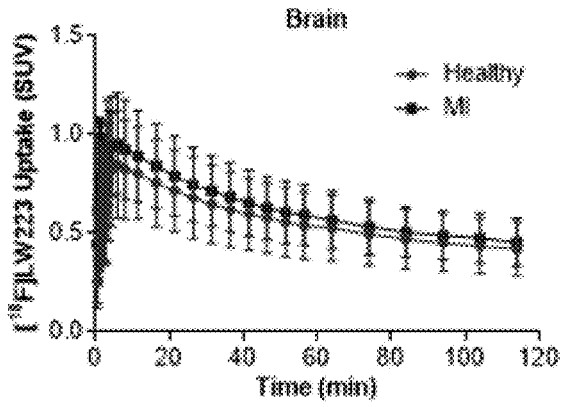
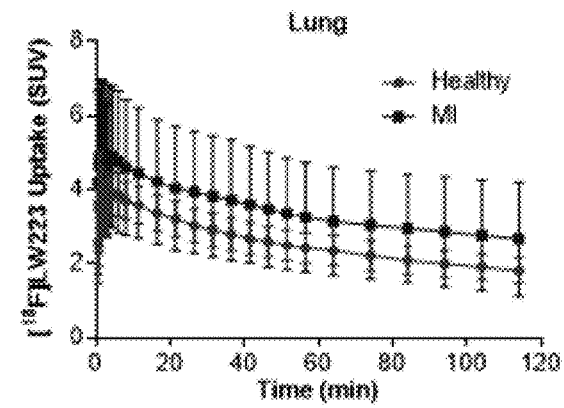
C
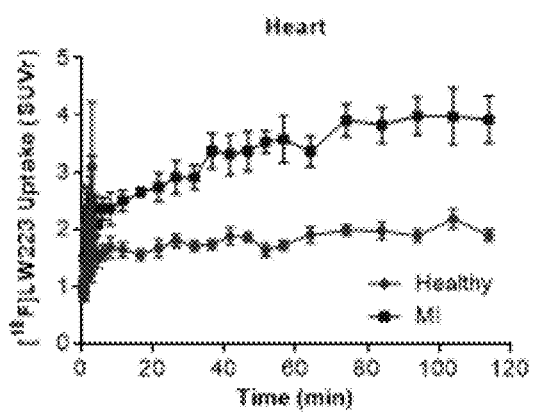
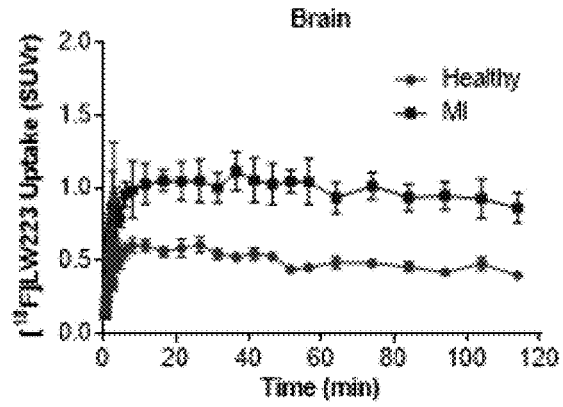
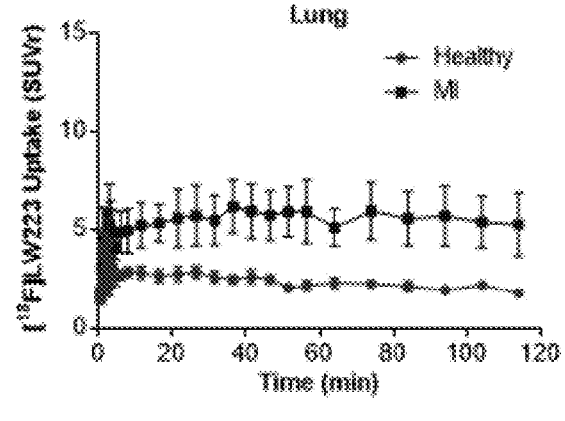

TSPO BINDERS

RELATED APPLICATION

The present case claims the benefit of and priority to GB 1810312.7 filed on 22 Jun. 2018, the contents of which are hereby incorporated by reference in their entirety.

FIELD OF THE INVENTION

The present invention provides compounds for use in binding to TSPO, methods for preparing those compound, methods for binding the compounds to TSPO, and methods for detecting the compound bound to TSPO.

BACKGROUND

The 18 kDa translocator protein (TSPO), formally known as the peripheral diazepine receptor (Papadopoulos et al.), is expressed within the outer membrane of the mitochondria and is involved in cholesterol transport and steroid synthesis (Lacapère). TSPO is highly expressed within inflammatory cells such as microglia in the brain (Wilms et al.; and Cosenza-Nashat et al.) and macrophages within the periphery (Fujimura et al.; and Bird et al.), and has therefore served as a marker of inflammation in pathologies throughout the body.

Increased expression of TSPO has been demonstrated in neurodegenerative diseases such as dementia and Parkinson's disease (Dupont et al.), as well as in cardiovascular disease, namely in atherosclerotic plaques (Bird et al.) and the heart post-myocardial infarction (Thackeray et al.). Therefore, a successful imaging approach targeting TSPO with PET has remarkable clinical value in a wide range of pathologies. In addition to serving as a marker of inflammation, recently, TSPO has also been demonstrated to have a role in neuroprotection (Thackeray et al.) and cardioprotection (Schalle et al.; and Paradis et al.), thus further expanding the range of applications of non-invasive TSPO imaging in the context of disease development and progression, as well as, target for disease-modifying therapies.

In the field of Positron Emission Tomography (PET) imaging of inflammation, TSPO is one of the most widely explored targets. The prototypical TSPO PET radiotracer, which was developed several decades ago, is $^{11}$C-PK11195 (Charbonneau et al.). This radiotracer has limited clinical routine dissemination due to the short half-life of the radioisotope (20 min) requiring hospitals to have an onsite cyclotron facility. In addition, $^{11}$C-PK11195 has relatively high non-specific binding (Chauveau et al.).

Therefore, considerable effort has been placed on the generation of novel families of TSPO radiotracers with improved characteristics, as summarized in a recently published review (Alam et al.). In spite of these developments, $^{11}$C-PK11195 is still regularly used as a clinical research tool. This is a result of the high inter-individual binding of all TSPO radiotracers synthesized and investigated after $^{11}$C-PK11195 development; which is now known to be caused by the genetic polymorphism rs6971, as identified in the seminal study by Owen et al. (Owen et al. *J. Cereb. Blood Flow Metab.* 2012). This common genetic polymorphism means that approximately 10% of the human population, classed as low affinity binders (LABs), are unimageable with second generation radiotracers, with the remainder of the human population split between mixed and high affinity binders (MABs and HABs) requiring genetic screening and complex post-imaging corrections. There are major variations in the susceptibility of second generation ligands to the rs6971 genetic polymorphism. For example, $^{11}$C-PBR28 has a LAB:HAB ratio in vitro of 55 (Owen et al. *J. Nucl. Med.*), whereas the more recently designed radiotracer $^{11}$C-ER176, an analogue of PK11195, has a ratio in vitro of 1.3 (Zanotti-Fregonara et al.).

To date therefore that PK11195 remains the only TSPO radiotracer to have robustly demonstrated an insensitivity to the rs6971 polymorphism in the human brain (Owen et al. *J. Nucl. Med.*; and Owen et al. *J. Cereb. Blood Flow Metab.* 2010). There is a need for further binders for TSPO that also demonstrate an insensitivity to the rs6971 polymorphism.

SUMMARY OF THE INVENTION

Generally the present invention provides compounds for use in binding the translocator protein (TSPO), thereby to act as tracers, such as radiotracers, for TSPO. The compounds of the invention may therefore find use in methods for detecting TSPO in vitro and in vivo. Such methods may be for use in the identification of inflammation, or for the diagnosis of diseases associated with altered TSPO levels, such as neurological inflammation, cancer and cardiovascular disease.

The compounds of the invention are insensitive to the rs6971 genetic polymorphism, and the compounds also exhibit an affinity for TSPO that is around twice that of the known TSPO binder, PK11195. The compounds of the invention have favourable kinetics in vivo, and a favourable dosimetric profile, and are therefore suitable for use in the clinic.

The in vivo characterisation of the compounds of the invention also reveals specific uptake consistent with TSPO expression. Blocking studies with a single concentration of PK11195 (1 mg/kg) confirmed target engagement, with a 64-81% reduction on the SUV values measured post-blocking compared with baseline scans.

The compounds of the invention may be regarded as ideally suited for use as labels for TSPO, such as radiolabels, for the reason that they have a nanomolar affinity for TSPO in both the human brain and heart, they are capable of brain penetration in vivo, they have a distribution profile in vivo is consistent with TSPO protein expression, their metabolism within plasma is slow and the level of metabolites recorded in tissues is low.

In a first aspect of the invention there is provided a compound of formula (I):

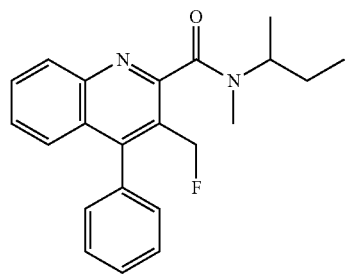 [SMILES: CCC(C)N(C)C(=O)c1nc2ccccc2c(-c2ccccc2)c1CF]

and salts, solvates and radiolabelled forms thereof.

In a preferred embodiment, the compound of formula (I) is a compound of formula (II):

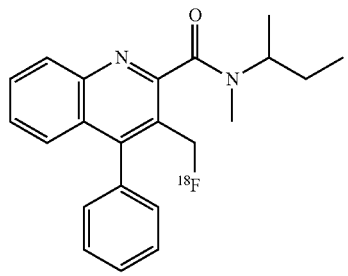 [SMILES: CCC(C)N(C)C(=O)c1nc2ccccc2c(-c2ccccc2)c1C[18F]]

and salts and solvates thereof.

TSPO binders bearing a fluorine radiolabel, such as the compounds of formula (II) have a longer half-life than those compounds bearing a carbon radiolabel, such as the compounds known in the art, including $^{11}$C-PK11195. The dosimetry profile of the compounds of formula (II) is such that the radiolabelled compounds are suitable for use with humans.

In a second aspect of the invention there is provided a method of preparing a compound of formula (I), the method comprising the step of substituting the bromine of a compound of formula (III) with fluorine:

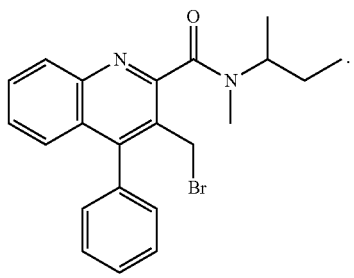 [SMILES: CCC(C)N(C)C(=O)c1nc2ccccc2c(-c2ccccc2)c1CBr]

In a third aspect of the invention there is provided a method of preparing a compound of formula (II), the method comprising the step of substituting the chlorine of a compound of formula (IV) with 18-fluorine:

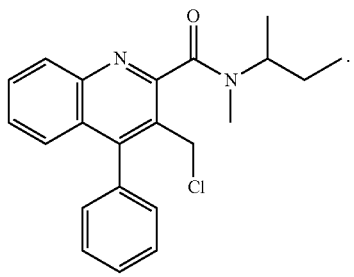 [SMILES: CCC(C)N(C)C(=O)c1nc2ccccc2c(-c2ccccc2)c1CCl]

The compound of formula (IV) is obtained or obtainable from the compound of formula (III) by substitution of the bromine of the compound of formula (III) with chlorine.

The invention also provides a composition comprising a compound of formula (I) together with one or more pharmaceutically acceptable excipients.

In a further aspect of the invention there is provided a method of detecting a compound of formula (I), the method comprising the step of contacting a compound of formula (I) with TSPO thereby to form a complex of the compound of formula (I) with TSPO, and detecting the compound of formula (I).

The TSPO may be provided in vitro or in vivo.

The compounds of the invention may be used to detect organ samples removed from a subject, such as heart and brain samples. Accordingly, the methods of the invention may be used to detect TSPO and to determine its levels, for example within the neurological and cardiovascular pathology.

In a further aspect of the invention there is provided a method for detecting a compound of formula (I) in a subject, the method comprising the step of administering a compound of formula (I) to a subject; and subsequently detecting the compound of formula (I).

Here, the subject may be a human subject.

The subject may be a subject that is known or suspected to have a disease that is associated with altered TSPO levels, such as raised TSPO levels, such as neurological inflammation, cancer and cardiovascular disease.

A subject may have a disease that is associated with altered TSPO levels, and the subject may be undergoing treatment for that disease. The method of the invention may be used to detect changes in TSPO levels, for example to gauge the effectiveness of the treatment. These and other aspects and embodiments of the invention are described in further detail below.

DETAILED DESCRIPTION

Figure 1:
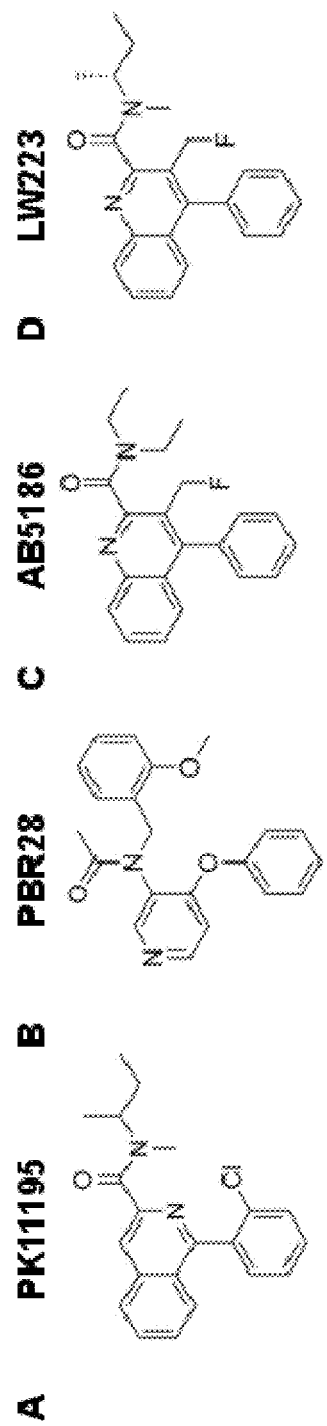
FIG. 1 shows the structures of known TSPO binders PK11195 (A), PBR28 (B) and AB5186 (C), and a TSPO binder according to an embodiment of the invention, LW223 (D). The compounds are shown in their cold (un-radiolabelled) forms.

The compounds of formula (I), including the compound of formula (II), find use as binders for TSPO. Accordingly, the compounds may be used to identify altered, such as increased, TSPO expression in subjects, such as humans, and may be used to identify those subjects at risk of, or having, a disease such as a neurological inflammation, cancer or a cardiovascular disease.

The compounds of the invention, and their synthesis and use are described in further detail below.

Stevenson et al. have previously described compound 11, which is a compound possessing an iodomethyl substituent to the quinoline ring, rather than the fluoromethyl group required by the compounds of the present case. This compound is for use in SPECT imaging of TSPO. Stevenson et al. do not describe compounds for use as radiotracers. Furthermore, this work does not suggest that such a compound, or any derivative, is or could be insensitive to the rs6971 genetic polymorphism.

Moreover, the reported binding data in Stevenson et al. teaches away from the use of the amide group substituents present in the compounds of the invention. Thus a comparison between compound 11 (where the amide nitrogen is methyl- and s-butyl-substituted) with related compound 18 (where the amide nitrogen is diethyl-substituted) shows that compound 18 has the best affinity for TSPO (see Table 1 of Stevenson et al.).

Blair et al. (*Chem. Sci.*) have previously described tracer-compounds 4 (which corresponds to compound 18 in Stevenson et al.), 5 and 6 (AB5186). The work by Blair et al. shows that the binding of iodo-compounds to TSPO is improved when the halogen is placed as a substituent on a pendant phenyl group, rather than present as a halomethyl substituent to the quinoline ring. Thus, the data in FIG. 2 in Blair et al. (*Chem. Sci.*) shows that compound 5 has better affinity than compound 4.

The present case shows that the compounds of the invention have better affinity than the compounds described by Blair et al. (*Chem. Sci.*), including compound 6, which is reference compound AB5186 in the present application.

Cappelli et al. (*J. Med. Lett.*) describes compounds and their uses that are related to those described by Stevenson et al. and Blair et al. (*Chem. Sci.*). This document says nothing about polymorphism binding issues.

WO 02/26713 focusses on compounds for use in treating parasitic infections. Some of the compounds disclosed have a very slight resemblance to compounds of the present case.

WO 02/26713 makes no mention of TSPO or radiotracing Compounds

The present invention provides a compound of formula (I):

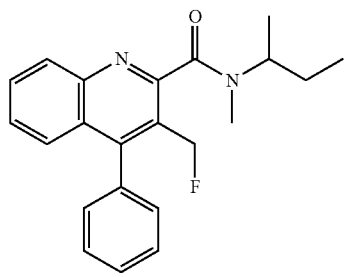 [SMILES: CCC(C)N(C)C(=O)c1nc2ccccc2c(-c2ccccc2)c1CF]

and salts, solvates and radiolabelled forms thereof.

It is preferred that the compound of formula (I) is:

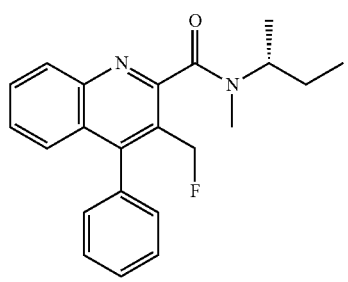 [SMILES: CC[C@@H](C)N(C)C(=O)c1nc2ccccc2c(-c2ccccc2)c1CF]

and salts, solvates and radiolabelled forms thereof.

The inventors have found that this particular stereoform—the (R)-configuration—has around a five-time greater affinity for TSPO compared with its enantiomer.

In a preferred embodiment, the compound is a compound of formula (II):

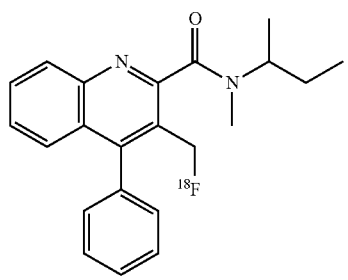 [SMILES: CCC(C)N(C)C(=O)c1nc2ccccc2c(-c2ccccc2)c1C[18F]]

and salts and solvates thereof.

The compound of formula (II) is a radiolabelled compound, and is more specifically labelled with the fluorine radioisotope, $^{18}$F.

It is preferred that the compound of formula (II) is:

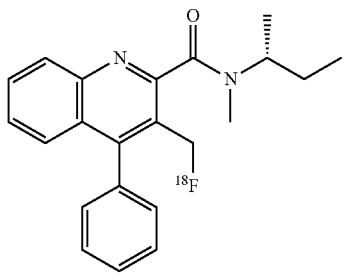 [SMILES: CC[C@@H](C)N(C)C(=O)c1nc2ccccc2c(-c2ccccc2)c1C[18F]]

and salts and solvates thereof.

The radiolabelled compound may be referred to as a hot compound, in contrast to a cold, non-radiolabelled compound.

Radioforms, Salts, Solvates, and Stereoforms

A compound of formula (I) or any other compound described herein, includes a compound where an atom is replaced by a naturally occurring or non-naturally occurring isotope. In one embodiment the isotope is a stable isotope. Thus a compound described here includes, for example deuterium containing compounds and the like. For example, H may be in any isotopic form, including $^{1}$H, $^{2}$H (D), and $^{3}$H (T); C may be in any isotopic form, including $^{11}$C, $^{12}$C, $^{13}$C, and $^{14}$C; O may be in any isotopic form, including $^{15}$O, $^{16}$O and $^{18}$O; F may be in any isotopic form, including $^{18}$F, and the like.

Typically the compounds of the invention contain a radioisotope that is suitable for detection (or imagining) by scintigraphic imaging methods, such as by positron emission tomography (PET), such as $^{18}$F, $^{11}$C, $^{13}$N or $^{15}$O. Thus, in one embodiment a compound of the invention contains a positron emitting radioisotope, such as $^{18}$F, $^{11}$C, $^{13}$N or $^{15}$O, and most preferably $^{18}$F.

In the preferred embodiments of the invention, the compounds of formula (I) the F atom may be provided as $^{18}$F. Such compounds are compounds of formula (II). These compounds are particularly useful radiotracers owing to their longer half-life (around 110 minutes) compared with those compounds having a $C^{11}$ radiolabel (around 20 minutes half-life).

Examples of salts of compound of formula (I), or any other compound described herein, include all pharmaceutically acceptable salts, such as, without limitation, acid addition salts of strong mineral acids such as HCl and HBr salts and addition salts of strong organic acids such as a methanesulfonic acid salt. Further examples of salts include sulfates and acetates such as acetate itself, trifluoroacetate or trichloroacetate.

A reference to a compound of formula (I) or any other compound described herein, is also a reference to a solvate of that compound. Examples of solvates include hydrates.

Unless otherwise specified, a reference to a particular compound includes isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

One aspect of the present invention pertains to compounds in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Compositions

The compounds of formula (I) and (II) are suitable for binding to TSPO and may do so in vivo. Accordingly, the compounds of formula (I) or (II) may be prepared in a composition for administration to the human or animal body.

Where the compounds of formula (I) are radiolabelled, they may be provided in a fluid composition at a concentration of at least 0.1, at least 0.5, at least 1, at least 2 or at least 5 MBq/mL.

Where the compounds of formula (I) are radiolabelled, they may be provided in a fluid composition at a concentration of at most 10, at most 20, at most 50, at most 100, at most 200, at most 300, or at most 200 MBq/mL.

The compounds may be used at a concentration in a range with the lower and upper limits selected from the values given above. For example, the compounds may be used at a concentration in the range 1 to 10 MBq/mL.

In some of the worked examples of the present case, $^{18}$F-LW223 is used at a concentration of 2 MBq/mL.

Typically the compounds of formula (I) and (II) are used in saline solutions, for example for intravenous injection.

While it is possible for the compound of formula (I) to be administered alone, it is desirable to present it as a pharmaceutical formulation (e.g., composition, preparation, medicament) comprising at least one compound of formula (I) as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

Thus, the present invention further provides compositions, as defined above, and methods of making a composition comprising admixing at least one compound of formula (I) as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 5th edition, 2005.

The formulations may be prepared by any methods well known in the art of pharmacy. Such methods include the step of bringing into association the compound of formula (I) with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), sprays, mists, or aerosols.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for intranasal administration, where the carrier is a liquid, include, for example, nasal spray, nasal drops, or by aerosol administration by nebuliser, include aqueous or oily solutions of the compound. As an alternative method of administration, a dry powder delivery may be used as an alternative to nebulised aerosols.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases. Additionally or alternatively, a formulation for pulmonary administration may be formulated for administration from a nebuliser or a dry powder inhaler. For example, the formulation may be provided with carriers or liposomes to provide a suitable particle size to reach the appropriate parts of the lung, to aid delivery of an appropriate does to enhance retention in the lung tissue.

Formulations suitable for parenteral administration (e.g., for example by injection or infusion, intravenously or subcutaneously), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, sugars, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 500 µg/mL, for example about 1 ng/mL to about 100 µg/mL, for example from about 10 ng/mL to about 10 µg/mL, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Methods of Preparation

The present invention also provides methods for the preparation of a compound of formula (I) and a compound of formula (II).

In the methods of preparation the fluorine in the compounds of formula (I) and (II) may be introduced in the last step in the synthesis. This is particularly important where the compounds of formula (I) contain fluorine as a radiolabel, such as in the compounds of formula (II). The methods for preparing the compounds of the invention do not require the handling of intermediate radiolabelled compounds, which is generally to be avoided, owing to the loss in radioactivity over time. Such would occur where the preparation and purification of radiolabelled intermediate compounds was required.

The compound of formula (I) may be prepared from a compound of formula (III), by substitution of the bromine in the compound of formula (III) with fluorine. The compound of formula (III) is:

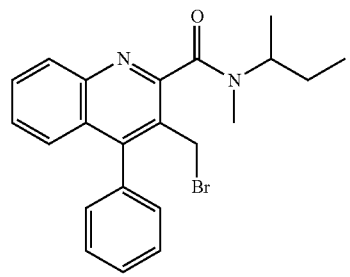 [SMILES: CCC(C)N(C)C(=O)c1nc2ccccc2c(-c2ccccc2)c1CCl]

and salts, solvates and radiolabelled forms thereof.

Halogen substitution reactions, and fluorine substitution reactions, are well known in the art.

The compound of formula (III) may be reacted with a fluorine anion to give the compounds of formula (I). The fluorine anion may be provided in the from a fluorine salt, such with an alkali metal salt, for example potassium fluoride. The substitution reaction may be performed in the presence of a catalyst, such as 18-crown-6.

The compound of formula (II) may be prepared from a compound of formula (IV), by substitution of the chlorine in the compound of formula (IV) with 19-fluorine. The compound of formula (IV) is:

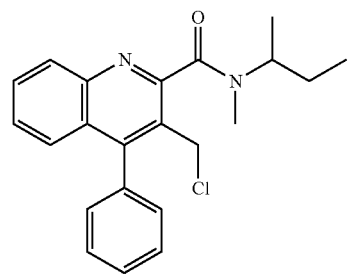

and salts, solvates and radiolabelled forms thereof.

For example, the compound of formula (IV) may be treated with $^{19}F$ anion, such as $[^{18}F]KF$, which is well known for use in the art to introduce the $^{18}F$ radiolabel.

The compound of formula (IV) may be prepared from the compound of formula (III), by substitution of the bromine in the compound of formula (IV) with chlorine.

For example, the compound of formula (IV) may be treated with chlorine anion, such as LiCl.

The present invention also provides the compounds of formula (III) and formula (IV), and salts, solvates and radiolabelled forms thereof.

Complex

In a further aspect of the invention there is provided a complex of a compound of formula (I) together with TSPO. Here, the compound of formula (I) is non-covalently bound to TSPO.

The complex of the compound of formula (I) with TSPO may be provided in vitro or in vivo. The TSPO may be present on the outer mitochondrial membrane.

Typically, the compound of formula (I) is provided in a binding pair with the TSPO. Thus, the stoichiometry of the compound and the TSPO in the complex is 1:1.

The compound of formula (I) may be detectable, such as where the compound is radiolabelled, when it is bound to TSPO in a complex.

Where a compound of formula (I) is radiolabelled, such as in the compounds of formula (II), the compound may be detected by methods appropriate to the radiolabel, such as positron emission tomography.

Where the compound of formula (I) is not radiolabelled it may be detected by other methods, including, for example, NMR.

TSPO is the translocator protein. It may be referred to as the peripheral benzodiazepine receptor.

The TPSO may be mammalian, such as human or rodent, TPSO.

The TSPO may be a protein comprising the NCBI Reference Sequence: NP_000705.2.

Methods and Uses

The compounds of the invention are for use in binding to TSPO. The compounds are detectable, and are detectable when present in complex with TSPO.

The compounds of the invention may be contacted with TSPO, which may be present in vivo or in vitro, to form a complex, such as described. The complex may then be detected, by detection of the compound of the invention.

Where the compound of formula (I) is radiolabelled, for example where the compound is a compound of formula (II), the compound may be detected by positron emission tomography (PET).

Thus, generally the methods of the present case include imaging the compounds of formula (I), such as those of formula (II), using scintigraphic imaging methods including PET (Positron Emission Tomography). Scintigraphic imaging methods may comprise the use of a camera or scanner to detect radioactivity in a single plane. PET imaging systems may comprise an array of detectors in a ring that also detect radioactivity in multiple dimensions.

Advantageously, the compounds of the invention are insensitive to mutations within TSPO, such as the rs6971 genetic polymorphism.

The method may include the step of administering a compound of formula (I) to a subject, such as a human or animal subject.

The methods of the invention may include the step of detecting a compound of formula (I), such as present in complex with TSPO, at a location in a subject selected from the group consisting of brain, heart, lungs, gall bladder, adrenal gland, kidney and gut.

The invention also provides a method of imaging TSPO expression in a subject, the method comprising the steps of administering a compound of formula (I), or a composition comprising the compound, to a subject, and producing one or more images of the distribution of the compound within the subject.

In some embodiments, the speed of onset and extent of TSPO expression, for example in relation to a neurological inflammation, may be determined using imaging. This may be useful, for example, in predicting the outcome of methods for treating the neurological inflammation.

Here, the binding of a compound of formula (I) at a site in the subject is indicative of the amount or extent of TSPO expression at the site.

The administration of a compound of formula (I) to a subject is described in more detail below.

One or more images of the distribution of the imaging agent within the subject may be produced using a molecular imaging technique, such as might make use of a radiolabel.

Using an appropriate molecular imaging technique, one or more images may be produced which show the distribution of the compound of formula (I) within all or part of the subject over a period of time after administration of the agent. The amount or concentration of detectable label in a tissue or region of the body is indicative of the amount of TSPO expression in the tissue or region. Increased concentrations of the compound of formula (I) in a tissue or region of the body are indicative that the cells in the tissue or region are undergoing increased TSPO expression, relative to other tissues or regions in the body. Imaging agents of the invention may therefore be useful in TSPO expression, and may be suitable for use in detecting diseases associated with altered levels of TSPO expression.

The subject may have a disease condition characterised by the presence of sites with elevated or reduced, such as elevated, TSPO expression, and the one or more images show the distribution of the compound of the invention at the one or more sites.

The invention also provides a method for determining the effectiveness of a therapy for a disease condition associated with elevated or reduced, such as elevated, TSPO expression, the method comprising the steps of:
administering a compound of formula (I), or a composition comprising the compound, to a subject before and during or after therapy; and,
producing one or more images of the distribution of the compound at the one or more sites of elevated or reduced, such as elevated, TSPO expression in the subject.

One or more images of the distribution of the compound of formula (I) at a site of TSPO expression in the subject during or after therapy may be produced.

A change, such as a decrease or increase, in binding of the compound of the invention at one or more sites of elevated or reduced after said therapy relative to before said therapy is indicative that the therapy is effective in alerting TSPO expression in the subject.

Where the disease condition is associated with elevated TSPO expression, the therapy may be regarded as effective if there is a decrease in binding of the compound at the one or more sites.

A compound of formula (I) may be used to assess drug efficacy in early stage clinical trials and subsequently in the clinic, where it could be used to guide treatment. Ineffective treatments could be abandoned at an early stage, allowing the selection of more effective drugs.

There is also provided a method for determining the efficacy of a treatment regimen for a subject, the method comprising:
subjecting the subject to an initial regimen of treatment, and;
determining the amount or extent of binding of a compound of formula (I) to TSPO in the subject,
wherein a change in the amount or extent of binding in response to the regimen is indicative that the regimen is efficacious in the subject.

This method may comprise the additional steps of:
altering the regimen of treatment and subjecting the subject to the altered regimen;
determining the amount or extent of binding of the compound of formula (I) to TSPO in the subject;
repeating the steps of altering the regimen and determining the binding until a change in the amount or extent of binding of the compound is observed,
wherein a change in the amount or extent of binding of the compound in response to the regimen is indicative that the regimen is efficacious in the subject.

In the methods above the subject may have a neurological inflammation and a decrease in the amount or extent of binding of the compound of formula (I) in response to the regimen is indicative that the regimen is efficacious in the subject.

The subject may have a disease condition characterised by increased levels of TSPO expression, and a decrease in the amount or extent of binding of the imaging agent to one or more disease sites in the subject in response to the regimen is indicative that the regimen is efficacious in the subject.

Dosage

Generally, the methods of the invention may comprise administering to a subject an effective amount of a compound of formula (I) so as to allow for effective labelling of TSPO in a target area.

It will be appreciated by one of skill in the art that appropriate dosages of the compound of formula (I), and compositions comprising the compound of formula (I), can vary from patient to patient. Determining the optimal dosage will generally involve the balancing of the level of the labelling of TSPO against any risk or deleterious side effects.

The selected dosage level will depend on a variety of factors including, but not limited to, the route of administration, the time of administration, the rate of excretion of the compound, the duration of the treatment, the use of drugs, compounds, and/or materials used by the subject, and the species, sex, age, weight, condition, general health, and prior medical history of the patient. The amount of compound of formula (I) and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the time required for labelling and detection. Methods of determining the most effective means and dosage of administration are well known to those of skill in the art and will vary with the formulation, the target cell(s) and/or organs, and the subject being treated. Single or multiple administrations can be carried out with the dose level and pattern being selected by the treating physician, veterinarian, or clinician.

In general, a suitable dose of a compound of formula (I) is in the range of about 10 µg to about 250 mg (more typically about 100 µg to about 25 mg) per kilogram body weight of the subject per day. Where the compound of formula (I) is a salt or a solvate, or the like, the amount administered is calculated on the basis of the parent compound and so the actual weight to be used is increased proportionately.

Where the compounds of formula (I) are radiolabelled, they may be used in an amount, such as in a dosage form, in an amount as set out below.

The compound may be used in an amount of at least 0.1, at least 0.5, at least 1, at least 5, at least 10 or at least 20 MBq.

The compound may be used in an amount of at most 50, at most 100, at most 200, at most 200, or at most 500 MBq.

The compounds may be used at an amount in a range with the lower and upper limits selected from the values given above. For example, the compounds may be used at an amount of 20 to 100 MBq.

The biological dose experienced by the subject may be low, such as 20 mSv per dosage, such as per scan. Preferably, the biological dose is 15 mSv per dosage or less, 10 mSv per dosage or less, such as 7 mSv per dosage or less.

Kits

The invention also provides to a kit comprising (a) a compound of formula (I) or a composition comprising a compound as defined in any one of formula (I), e.g., typically provided in a suitable container and/or with suitable packaging; and (b) instructions for use, e.g., written instructions on how to administer the compound or composition.

Routes of Administration

A compound of formula (I), or a composition comprising the compound of formula (I), may be administered to a subject by any convenient route of administration, whether systemically/peripherally or topically (i.e., at the site of desired action).

Routes of administration include, but are not limited to, pulmonary (e.g., by inhalation or insufflation using, e.g., via an aerosol, e.g., through the mouth or nose); parenteral, for example, by injection or infusion, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Subject

A compound of formula (I) may be administered to a subject, for the detection of TSPO, including the levels of TSPO expression and the distribution of TSPO expression.

The subject may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orang-utan, gibbon), or a human. Furthermore, the subject may be any of its forms of development, for example, a foetus. The subject may be a craniate, such as an aquatic craniate, such as fish (e.g. zebrafish).

It is also envisaged that the invention may be practised on a non-human animal. A non-human mammal may be a rodent. Rodents include rats, mice, guinea pigs, chinchillas and other similarly-sized small rodents used in laboratory research.

In one embodiment, the subject is a human, such as an adult human.

In one embodiment, the subject is a rodent, such as a mouse.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXPERIMENTAL AND RESULTS

General Experimental

All reagents and starting materials were obtained from commercial sources and used as received. All dry solvents were purified using a PureSolv 500 MD solvent purification system. All reactions were performed under argon unless otherwise stated. Brine is defined as a saturated solution of aqueous sodium chloride.

Flash column chromatography was carried out using Fisher Matrix silica 60. Macherey-Nagel aluminium-backed plates pre-coated with silica gel 60 (UV254) were used for thin layer chromatography and were visualized using UV light.

$^1$H NMR and $^{13}$C NMR spectra were recorded on a Bruker DPX 400 spectrometer or Bruker 500 spectrometer with chemical shift values in ppm relative to tetramethylsilane ($\delta_H$ 0.00 and $\delta_c$ 0.0) or residual chloroform ($\delta_H$ 7.26 and $\delta_c$ 77.2) as the standard. $^1$H and $^{13}$C assignments are based on two-dimensional COSY and DEPT experiments, respectively.

Infrared spectra were recorded on a JASCO FTIR 410 spectrometer.

Mass spectra were recorded using electron impact, chemical ionisation or fast atom bombardment techniques. HRMS spectra were recorded using a dual-focusing magnetic analyser mass spectrometer.

Melting points were determined on a Gallenkamp melting point apparatus.

Chiral HPLC methods were calibrated with the corresponding racemic mixtures.

3-Methyl-4-phenylquinoline-2-carboxylic acid was prepared as previously reported (Stevenson et al.).

Compound Preparation

A compound of formula (I) was prepared as shown in the scheme below. The compound is known as LW223.

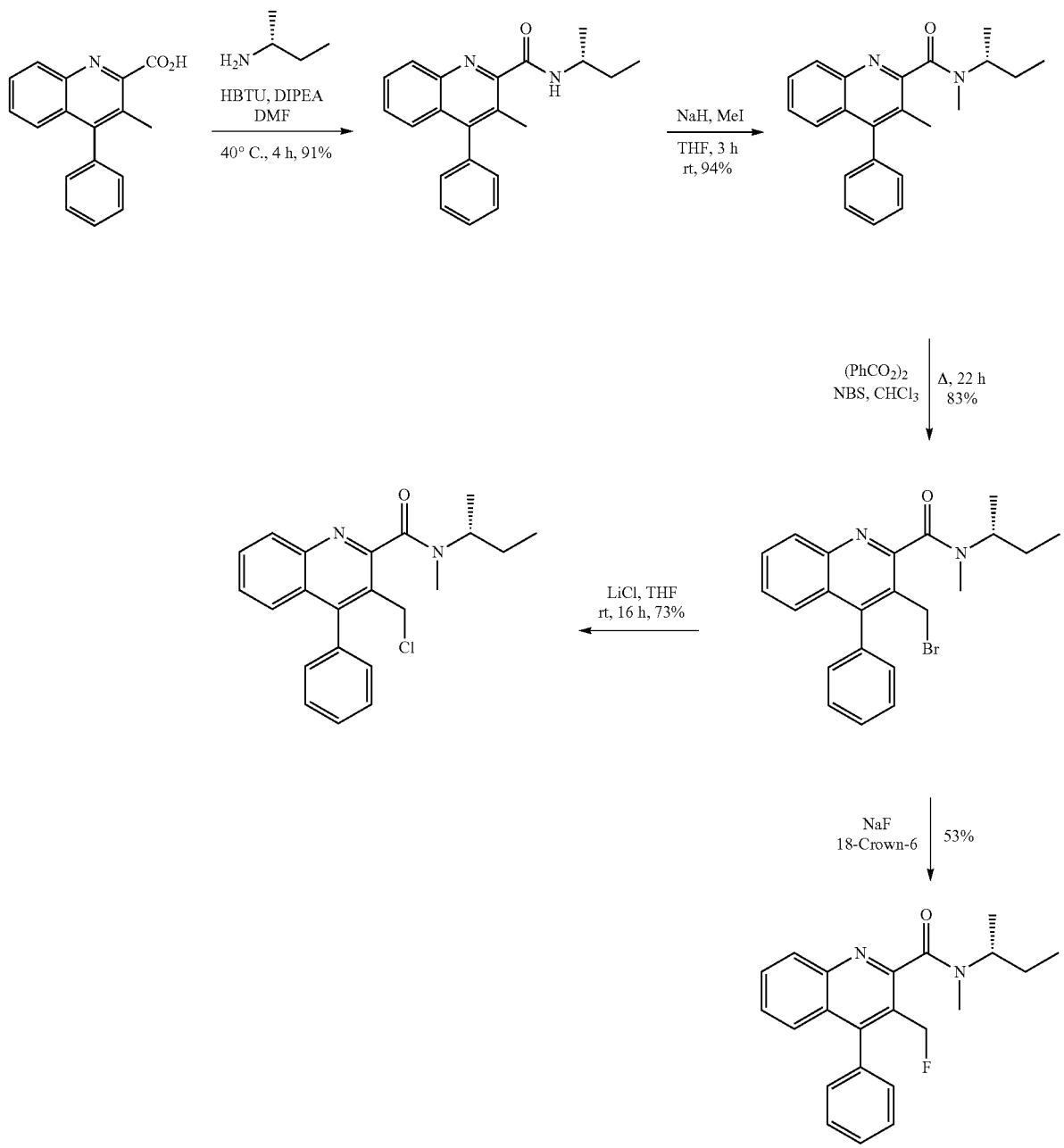

Scheme 1 - Preparation of LW223

(R)-(N-sec-Butyl)-3-methyl-4-phenylquinoline-2-carboxamide

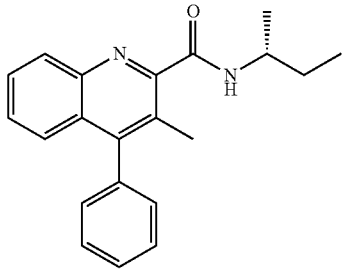 [SMILES: CC[C@@H](C)NC(=O)c1nc2ccccc2c(-c2ccccc2)c1C]

To a solution of 3-methyl-4-phenylquinoline-2-carboxylic acid (2.54 g, 9.65 mmol) in anhydrous N,N-dimethylformamide (250 mL) was added O-(benzotriazol-1-yl)-N,N,N',N'-tetramethyluronium hexafluorophosphate (5.49 g, 14.5 mmol) and N,N'-diisopropylethylamine (3.40 mL, 19.3 mmol). The reaction mixture was stirred at room temperature for 0.5 h before the addition of (R)-(−)-sec-butylamine (1.10 mL, 10.6 mmol) and then heated to 40° C. for 4 h. The reaction mixture was cooled to room temperature, diluted with ethyl acetate (300 mL) and washed with water (3×200 mL) and brine (200 mL). The organic layer was dried (MgSO$_4$), filtered and concentrated in vacuo to give a brown oil. Purification by flash column chromatography (petroleum ether/ethyl acetate, 4:1) gave (R)-(N-sec-butyl)-3-methyl-4-phenylquinoline-2-carboxamide as a white solid (2.81 g, 91%).

Mp 152-154° C. (lit. mp 157-158° C.—see Cappelli et al. (*J. Med. Chem.*)); IR (KBr) 3287 (NH), 2968 (CH), 1641 (CO), 1539, 1448, 1157, 761 cm$^{-1}$; $[\alpha]_D^{25}$−26.7 (c 1.0, CHCl$_3$); $^1$H NMR (400 MHz, CDCl$_3$) δ 1.03 (3H, t, J=7.4 Hz, CHCH$_2$CH$_3$), 1.33 (3H, d, J=6.6 Hz, CHCH$_3$), 1.61-1.75 (2H, m, CH$_2$CH$_3$), 2.56 (3H, s, 3-CH$_3$), 4.08-4.20 (1H, m, CHCH$_3$), 7.21-7.25 (2H, m, ArH), 7.35 (1H, d, J=8.3 Hz, ArH), 7.40-7.55 (4H, m, ArH), 7.65 (1H, ddd, J=8.3, 6.8, 1.4 Hz, ArH), 7.90 (1H, d, J=8.3 Hz, NH), 8.09 (1H, d, J=8.3 Hz, ArH); $^{13}$C NMR (101 MHz, CDCl$_3$) δ 10.6 (CH$_3$), 17.6 (CH$_3$), 20.5 (CH$_3$), 29.9 (CH$_2$), 46.8 (CH), 126.1 (CH), 127.5 (CH), 127.9 (CH), 128.6 (C), 128.6 (2×CH), 128.7 (CH and C), 129.3 (2×CH), 129.5 (CH), 137.3 (C), 144.7 (C), 149.5 (C), 150.1 (C), 166.2 (C); MS (C) m/z 319 (M+H$^+$, 100%), 220 (19), 202 (5), 148 (6), 113 (16), 85 (77); HRMS (C) calcd for C$_{21}$H$_{23}$N$_2$O (M+H$^+$), 319.1810, found 319.1809.

(R)-(N-sec-Butyl)-N-methyl-3-methyl-4-phenylquinoline-2-carboxamide

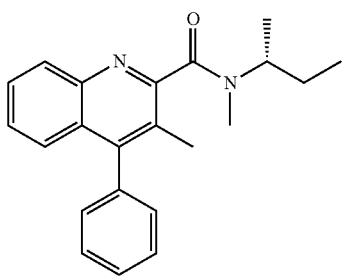 [SMILES: CC[C@@H](C)N(C)C(=O)c1nc2ccccc2c(-c2ccccc2)c1C]

To a solution of (R)-(N-sec-butyl)-3-methyl-4-phenylquinoline-2-carboxamide (2.81 g, 8.82 mmol) in tetrahydrofuran (176 mL) was added sodium hydride (60% dispersion in mineral oil, 0.710 g, 17.6 mmol). The mixture was stirred at room temperature for 0.5 h, before the addition of iodomethane (2.75 mL, 44.1 mmol). The resultant solution was stirred at room temperature for 3 h and then quenched by addition of water. The aqueous phase was extracted with diethyl ether (3×10 mL). The combined organic phases were washed with a 10% aqueous solution of sodium thiosulfate (10 mL), brine (10 mL), dried (Na$_2$SO$_4$), filtered and concentrated in vacuo. Purification by flash column chromatography (petroleum ether/ethyl acetate, 3:1) gave (R)-(N-sec-butyl)-N-methyl-3-methyl-4-phenylquinoline-2-carboxamide as a white solid (2.75 g, 94%).

NMR spectra showed a 1:1 mixture of rotamers. Signals for both rotamers are recorded. Mp 114-117° C. (lit. mp 117-118° C.—see Cappelli et al. (*J. Med. Chem.*)); IR (KBr) 2969 (CH), 1637 (CO), 1466, 1072, 731 cm$^{-1}$; $[\alpha]_D^{23}$−6.3 (c 1.0, CHCl$_3$); $^1$H NMR (400 MHz, CDCl$_3$) δ 0.86 (3H, t, J=7.3 Hz, CH$_2$CH$_3$), 1.03 (3H, t, J=7.3 Hz, CH$_2$CH$_3$), 1.24 (3H, d, J=6.6 Hz, CHCH$_3$), 1.28 (3H, d, J=6.6 Hz, CHCH$_3$), 1.36-1.71 (4H, m, 2×CH$_2$CH$_3$), 2.21 (3H, s, 3-CH$_3$), 2.23 (3H, s, 3-CH$_3$), 2.73 (3H, s, NCH$_3$), 3.04 (3H, s, NCH$_3$), 3.42-3.53 (1H, m, CHCH$_3$), 4.84-4.94 (1H, m, CHCH$_3$), 7.25-7.31 (4H, m, ArH), 7.38-7.44 (4H, m, ArH), 7.45-7.57 (6H, m, ArH), 7.60-7.67 (2H, m, ArH), 8.09 (1H, d, J=8.3 Hz, ArH), 8.11 (1H, d, J=8.3 Hz, ArH); $^{13}$C NMR (101 MHz, CDCl$_3$) δ 11.2 (CH$_3$), 11.3 (CH$_3$), 16.0 (CH$_3$), 16.4 (CH$_3$), 17.3 (CH$_3$), 18.6 (CH$_3$), 25.5 (CH$_3$), 26.5 (CH$_3$), 27.2 (CH$_2$), 29.3 (CH$_2$), 49.6 (CH), 55.8 (CH), 124.6 (C), 125.3 (C), 125.9 (CH), 126.0 (CH), 126.7 (2×CH), 126.8 (2×CH), 127.4 (2×C), 128.0 (2×CH), 128.6 (2×CH), 128.7 (2×CH), 129.2 (4×CH), 129.4 (2×CH), 136.7 (C), 136.8 (C), 145.8 (C), 146.1 (C), 148.0 (C), 148.1 (C), 156.1 (C), 156.6 (C), 169.4 (C), 169.7 (C); MS (C) m/z 333 (M+H$^+$, 100%), 291 (48), 250 (41), 220 (14), 86 (23); HRMS (C) calcd for C$_{22}$H$_{25}$N$_2$O (M+H$^+$), 333.1967, found 333.1972.

(R)-3-Bromomethyl-(N-sec-butyl)-N-methyl-4-phenylquinoline-2-carboxamide

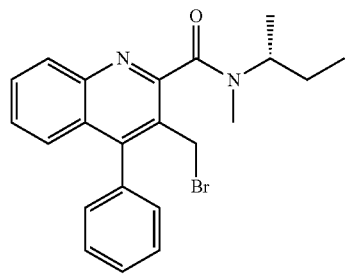 [SMILES: CC[C@@H](C)N(C)C(=O)c1nc2ccccc2c(-c2ccccc2)c1CBr]

To a stirred, degassed solution of (R)-(N-sec-butyl)-N-methyl-3-methyl-4-phenylquinoline-2-carboxamide (2.70 g, 8.12 mmol) in chloroform (300 mL) was added N-bromosuccinimide (2.17 g, 12.2 mmol) and dibenzoyl peroxide (0.20 g, 0.812 mmol) and the solution heated under reflux for 6 h. A further portion of N-bromosuccinimide (1.00 g, 5.61 mmol) was then added and the solution heated under reflux for a further 16 h. The reaction mixture was cooled to room temperature, filtered and the solvent removed in vacuo. The crude residue was then diluted with ethyl acetate (100 mL) and washed with water (3×100 mL). The organic layer was dried (MgSO$_4$), filtered and concentrated in vacuo. Purification by flash column chromatography using a graduated eluent of dichloromethane>dichloromethane/ethyl acetate (95:5) afforded (R)-3-bromomethyl-(N-sec-butyl)-N-methyl-4-phenylquinoline-2-carboxamide as an orange solid (2.76 g, 83%).

NMR spectra showed a 2:1 mixture of rotamers. Only signals for the major rotamer are recorded. Mp 160-164° C.; IR (KBr) 2970 (CH), 1631 (CO), 1484, 1397, 1046, 766 cm$^{-1}$; $[\alpha]_D^{28}$ −9.0 (c 1.0, CHCl$_3$); $^1$H NMR (400 MHz, CDCl$_3$) δ 1.09 (3H, t, J=7.4 Hz, CH$_2$CH$_3$), 1.32 (3H, d, J=6.8 Hz, CHCH$_3$), 1.51-1.80 (2H, m, CH$_2$CH$_3$), 2.86 (3H, s, NCH$_3$), 4.60 (1H, d, J=10.2 Hz, 3-CHH), 4.67 (1H, d, J=10.2 Hz, 3-CHH), 4.87 (1H, sextet, J=6.8 Hz, CHCH$_3$), 7.37-7.48 (4H, m, ArH), 7.51-7.59 (3H, m, ArH), 7.70 (1H, ddd, J=8.3, 6.7, 1.5 Hz, ArH), 8.10 (1H, dd, J 8.8, 8.3 Hz, ArH); $^{13}$C NMR (101 MHz, CDCl$_3$) δ 11.1 (CH$_3$), 17.1 (CH$_3$), 26.6 (CH$_2$), 27.7 (CH$_2$), 30.5 (CH$_3$), 50.1 (CH), 126.3 (C), 126.7 (2×CH), 127.4 (CH), 128.6 (2×CH), 128.7 (CH), 129.0 (CH), 129.1 (CH), 129.5 (CH), 130.1 (C), 134.9 (C), 146.4 (C), 149.3 (C), 156.0 (C), 168.4 (C); MS (EI) m/z 410 (M$^+$, 5%), 298 (15), 296 (14), 217 (57), 189 (28), 151 (10), 86 (100); HRMS (EI) calcd for C$_{22}$H$_{23}$$^{79}$BrN$_2$O (M$^+$), 410.0994, found 410.0992.

(R)-(N-sec-Butyl)-3-chloromethyl-N-methyl-4-phenylquinoline-2-carboxamide

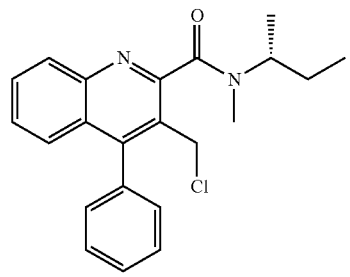 [SMILES: CC[C@@H](C)N(C)C(=O)c1nc2ccccc2c(-c2ccccc2)c1CCl]

To a solution of (R)-3-bromomethyl-(N-sec-butyl)-N-methyl-4-phenylquinoline-2-carboxamide (0.500 g, 1.22 mmol) in dry tetrahydrofuran (10 mL) was added lithium chloride (0.160 g, 3.66 mmol) and the reaction mixture stirred at room temperature for 16 h. The reaction was quenched with water (30 mL) and extracted into ethyl acetate (3×30 mL). The organic layers were combined and washed with brine (90 mL), dried (MgSO$_4$), filtered and concentrated in vacuo. The product was purified by flash column chromatography (dichloromethane/ethyl acetate, 95:5) to afford (R)-3-chloromethyl-(N-sec-butyl)-N-methyl-4-phenylquinoline-2-carboxamide as a white solid (0.327 g, 73%).

NMR spectra showed a 1.5:1 mixture of rotamers. Only signals for the major rotamer are recorded. Mp 140-142° C.; IR (neat) 2970 (CH), 1620 (CO), 1481, 1404, 1219, 748 cm$^{-1}$; $[\alpha]_D^{24}$ −11.6 (c 1.0, CHCl$_3$); $^1$H NMR (400 MHz, CDCl$_3$) δ 1.08 (3H, t, J=7.4 Hz, CH$_2$CH$_3$), 1.30 (3H, d, J=6.8 Hz, CHCH$_3$), 1.49-1.79 (2H, m, CH$_2$CH$_3$), 2.84 (3H, s, NCH$_3$), 4.67 (1H, d, J=10.6 Hz, 3-CHH), 4.72 (1H, d, J=10.6 Hz, 3-CHH), 4.82-4.92 (1H, m, CHCH$_3$), 7.36-7.61 (7H, m, ArH), 7.69-7.75 (1H, m, ArH), 8.11 (1H, dd, J 9.0, 8.4 Hz, ArH); $^{13}$C NMR (101 MHz, CDCl$_3$) δ 11.1 (CH$_3$), 17.1 (CH$_3$), 26.6 (CH$_2$), 30.4 (CH$_3$), 40.4 (CH$_2$), 50.1 (CH), 125.8 (C), 126.8 (CH), 127.2 (C), 127.4 (CH), 128.5 (2×CH), 128.7 (CH), 129.4 (CH), 129.6 (2×CH), 130.1 (CH), 134.9 (C), 146.6 (C), 149.5 (C), 156.1 (C), 168.5 (C); MS (ESI) m/z 389 (M+Na$^+$, 100%); HRMS (ESI) calcd for C$_{22}$H$_{23}$$^{35}$ClN$_2$NaO (M+Na$^+$), 389.1391, found 389.1381.

LW223—(R)-(N-sec-Butyl)-3-fluoromethyl-N-methyl-4-phenylquinoline-2-carboxamide

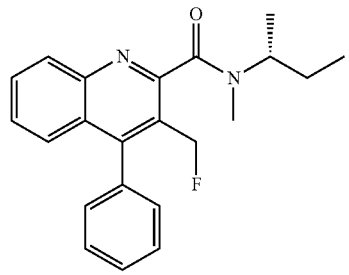 [SMILES: CC[C@@H](C)N(C)C(=O)c1nc2ccccc2c(-c2ccccc2)c1CF]

To a solution of 18-crown-6 (0.032 g, 0.12 mmol) in acetonitrile (2.5 mL) was added potassium fluoride (0.036 g, 0.61 mmol) and the resulting suspension stirred at room temperature for 0.5 h. A solution of (R)-3-bromomethyl-(N-sec-butyl)-N-methyl-4-phenylquinoline-2-carboxamide (0.050 g, 0.12 mmol) in acetonitrile:dichloromethane (2:1, 9.0 mL) was then added dropwise and the reaction mixture heated under reflux for 72 h. Upon completion, the reaction mixture was cooled to ambient temperature and water (20 mL) was added. The solution was extracted with dichloromethane (3×20 mL), dried (MgSO$_4$), filtered and concentrated in vacuo. Purification by flash column chromatography (petroleum ether/ethyl acetate 7:3) gave (R)-N-(sec-butyl)-3-(fluoromethyl)-N-methyl-4-phenylquinoline-2-carboxamide as a white solid (0.023 g, 53%).

NMR spectra showed a 3:1 mixture of rotamers. Only signals for the major rotamer are recorded. Mp 146-148° C.; IR (neat) 2972 (CH), 1628 (CO), 1559, 1485, 1398, 1049, 970 cm$^{-1}$; $[\alpha]_D^{30}$ −12.6 (c 0.5, CHCl$_3$); $^1$H NMR (400 MHz, CDCl$_3$) δ 1.05 (3H, t, J=7.4 Hz, CH$_2$CH$_3$), 1.29 (3H, d, J=6.8 Hz, CHCH$_3$), 1.41-1.78 (2H, m, CH$_2$CH$_3$), 2.77 (3H, s, NCH$_3$), 4.84-4.95 (1H, m, NCH), 5.31 (1H, dd, J 20.8, 10.8 Hz, 3-CHH), 5.44 (1H, dd, J 20.8, 10.8 Hz, 3-CHH), 7.31-7.40 (2H, m, ArH), 7.43-7.58 (5H, m, ArH), 7.74 (1H, t, J 7.6 Hz, ArH), 8.17 (1H, d, J 8.4 Hz, ArH); $^{13}$C NMR (101 MHz, CDCl$_3$) δ 10.9 (CH$_3$), 17.4 (CH$_3$), 26.5 (CH$_3$), 29.9 (CH$_2$), 50.0 (CH), 79.2 (CH$_2$, $^1J_{C-F}$=162.8 Hz), 123.0 (C, $^2J_{C-F}$=15.1 Hz), 127.0 (CH), 127.1 (C, $^4J_{C-F}$=2.3 Hz), 127.4 (CH, $^5J_{C-F}$=1.2 Hz), 128.5 (2×CH), 128.7 (CH), 129.6 (2×CH), 129.7 (CH), 130.4 (CH), 134.8 (C, $^4J_{C-F}$=1.5 Hz), 147.4 (C, $^3J_{C-F}$=2.5 Hz), 150.8 (C, $^3J_{C-F}$=4.7 Hz), 156.6 (C, $^5J_{C-F}$=2.1 Hz), 168.8 (C); MS (ESI) m/z 373 (M+Na$^+$, 100%); HRMS (ESI) calcd for C$_{22}$H$_{23}$FN$_2$NaO (M+Na$^+$), 373.1687, found 373.1670.

Enantiomeric excess was determined by HPLC analysis with a chiralcel AD-H column (hexane: $^i$PrOH 97.5:2.5, flow rate 1.0 mL/min), t$_{major}$=30.68 and 32.22 min, t$_{minor}$=27.15 and 38.38 min; er=99.5:0.5.

A compound of formula (II) was prepared as shown in the scheme below. The compound is known as $^{19}$F-LW223.

Scheme 2 - Preparation of $^{18}$F-LW223

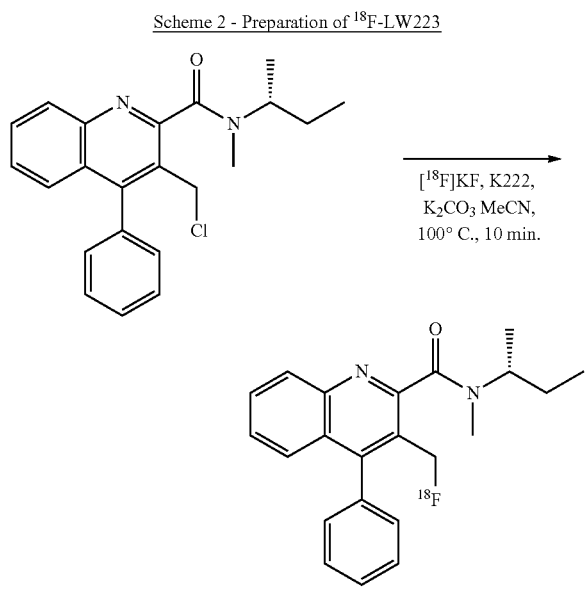

$^{18}$F-LW223—(R)-(N-sec-Butyl)-3-[19-fluoro]-methyl-N-methyl-4-phenylquinoline-2-carboxamide (R)-(N-sec-Butyl)-3-chloromethyl-N-methyl-4-phenylquinoline-2-carboxamide was reacted with $^{18}$F-fluoride ([$^{18}$F]KF)) in the presence of potassium carbonate and Kryptofix 222 at 100° C. for 10 min. using a commercial synthesizer, GE TRACERlab® FX-FN. The radiolabeled product was purified by semi-preparative High-Performance Liquid Chromatography (HPLC) using the following conditions: C18 Synergi Hydro-RP 80 Å, 150×10 mm, 4 μm column (Phenomenex, UK), acetonitrile/water (70:30 v/v) with a flow rate of 3 mL/min.

The final product was formulated in a physiological solution containing 10% ethanol in normal saline. $^{18}$F-LW223 was obtained with an average non-decay corrected yield of 35% (starting from 15±5 GBq of $^{18}$F-fluoride, n=20) after a total synthesis time of 55 minutes. The identity of $^{18}$F-LW223, radiochemical purity (>99%) and specific activity (410-810 GBq/μmol; 11-22 Ci/μmol) were determined by HLPC analysis at the end of the synthesis.

Biological Testing
In Vitro Competition and Saturation Binding Assays with Human Tissue All studies using human tissue were conducted in accordance with the East of Scotland Research Ethics Service (Edinburgh Brain Bank, 11/ES/0022). Fifty-one brain (78% male, age 53.9±9.5) and twenty-nine heart (83% female, age 48.2±13.2) samples were obtain and screened for the rs6971 genetic polymorphism and grouped into high affinity binders (HAB), mixed affinity binders (MAB) or low affinity binders (LAB) as previously described (Owen et al. *J. Cereb. Blood Flow Metab.* 2012). To exclude sex dependent differences in TSPO binding (Fairweather et al.), only male samples were utilized in this study. Sample tissues were homogenized in 10× w/v buffer (50 mM Tris-Base, pH 7.4, 4° C.) before centrifugation (32,000 g, 10 min, 4° C.). Tissue pellets were then resuspended in 10× w/v buffer and centrifuged again before re-suspending them in buffer (2 mL). Samples were then assessed for protein concentration using the Bio-Rad protein assay (Bio-Rad, USA), aliquoted and stored at −80° C. until use.

Competition binding assays were carried out as previously reported (Blair et al. (*Med. Chem. Commun.*)). Briefly, 250 μg protein/mL of each sample was prepared in buffer, then 200 μL of this solution was added to 100 μL of 1 nM $^{3}$H-PK11195 (PerkinElmer, USA), together with 100 μL of our test ligands PK11195 (Sigma-Aldrich, USA), PBR28 (ABX, Germany), AB5186 or LW223 at 14 different concentrations (ranging from 0.001-3,000 nM) for 90 min at 4° C. A concentration of 8 μM was used to determine non-specific binding for each ligand. Binding was terminated with the addition of 2 mL of ice cold buffer before being immediate filtered over a Whatman GF/B filters (Whatman, UK) pre-treated with 0.3% polyethylenimine (Sigma-Aldrich, USA) using a Brandel harvester (Brandel, USA). Filter paper was then removed, placed into 2.5 mL of Optiphase HiSafe 3 (Perkin Elmer, USA) and counted 48 hours later on a Hidex 300 SL (Hidex, Finland). Saturation assays were performed to determine the $K_d$ of PK11195 using a similar protocol, with the exception that 6 concentrations of $^{3}$H-PK11195 (1.6-200 nM) was used alongside 10 μM of PK11195 to determine nonspecific binding. All binding assays were performed in triplicate. GraphPad Prism version 6 (GraphPad Software, USA) was used to fit all binding affinity curves. A comparison of a one-site and two-site fitting was made using the least squares algorithm and model selection was compared using an F test. The null hypothesis (that one-site fitting as more suitable) was rejected if p<0.05. The mean % SB normalized to the minimum inhibition of each group (HAB, MAB or LAB) was used to determine whether a one-site or two-site fitting was appropriate, and to subsequently calculate LAB:HAB ratio. Affinity values ($K_i$) were calculated by fitting individual tissue samples based on the mean group fitting. A PK11195 $K_d$ value of 13.95 nM was used based on saturation binding curves results.

Comments

Figure 7:
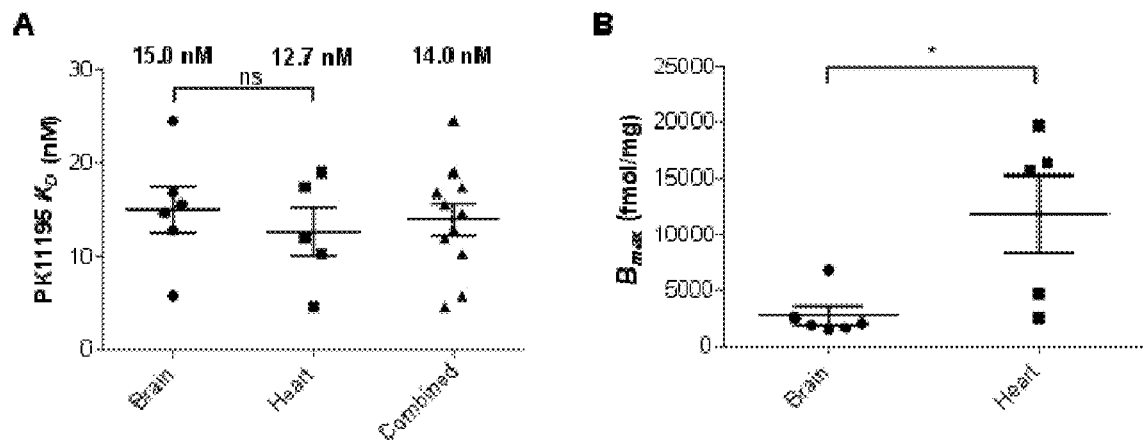
FIG. 7 shows the dissociation constant ($K_d$) values and maximal binding ($B_{max}$) of PK11195 in human brain and heart, where (a) shows the $K_d$ values of PK11195 and (b) shows the $B_{max}$ calculated from saturation binding assays. The results represent the mean±S.E.M., brain n=6, heart n=5, ns=not significant, *=p<0.05 using an unpaired t-test for brain vs. heart.

Competition binding assays were used to calculate the affinity ($K_i$) of the established TSPO ligands PK11195 and PBR28, as well as our ligands AB5186 and LW223 (as shown in FIG. 1) in order to assess their susceptibility to the genetic polymorphism. Saturation assays were performed to determine the $K_d$ of PK11195 using our experimental conditions, which was 13.95 nM (see FIG. 7).

Figure 2:
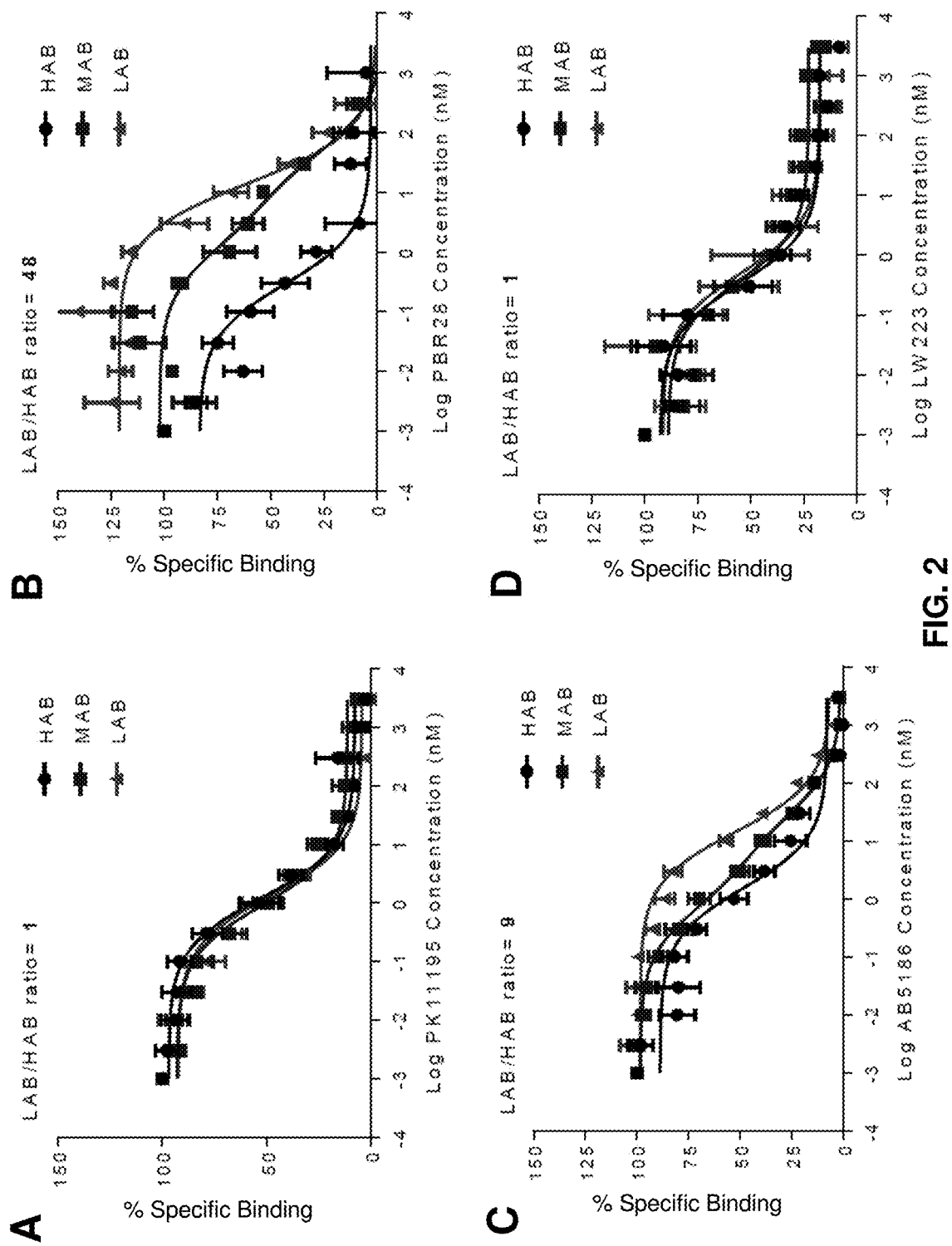
FIG. 2 shows the binding affinity of TSPO ligands in human brains from high (HAB), mixed (MAB) and low (LAB) affinity binders, where (a) shows the mean PK11195 binding affinity curves plotted using a one-site fitting, HAB n=6, MAB n=8 and LAB n=4; (b) shows the mean PBR28 binding affinity curves plotted using a one-site fitting apart from MAB where a two-site fitting was used, HAB n=4, MAB n=5 and LAB n=4; (c) shows the mean AB5186 binding affinity curves plotted using a one-site fitting apart from MAB where a two-site fitting was used, HAB n=6, MAB n=6 and LAB n=5; (d) shows the mean LW223 binding affinity curves plotted using a one-site fitting, HAB n=5, MAB n=5 and LAB n=4; and (e) shows the individually calculated affinity values ($K_i$) for PK11195 against each human sample, which values were also calculated for (f) PBR28, (g) AB5186 and (h) LW223. ns=not significant, *=p<0.05, ***=p≤0.001 using an unpaired t-test for HAB vs. LAB. All results represent the mean±SEM.

In competition binding assays using human brain, PK11195 was not affected by the genetic polymorphism, with a LAB:HAB affinity ratio of 1 (FIG. 2(*a*)), unlike PBR28 which had a ratio of 49 (FIG. 2(*b*)). The ligand AB5186 was affected by the genetic polymorphism with a ratio of 9 (FIG. 2(*b*)), unlike LW223, which was not affected and had a ratio of 1. Individually calculated affinity values for all brain samples demonstrated no significant difference between HAB and LAB in PK111195 and LW223 binding studies (FIGS. 2(*e*) and (*h*) H respectively). The mean affinity of LW223 was 0.6 nM, which was 2 times higher than PK11195. Comparison of individually calculated affinity values in HAB and LAB for PBR28 and AB5186 revealed a significant difference between groups (FIGS. 2(*f*) and (*g*)). The MAB group in PBR28 and AB5186 suited a two-site fitting, whereas all other experiments were more suited to one-site fitting.

Figure 3:
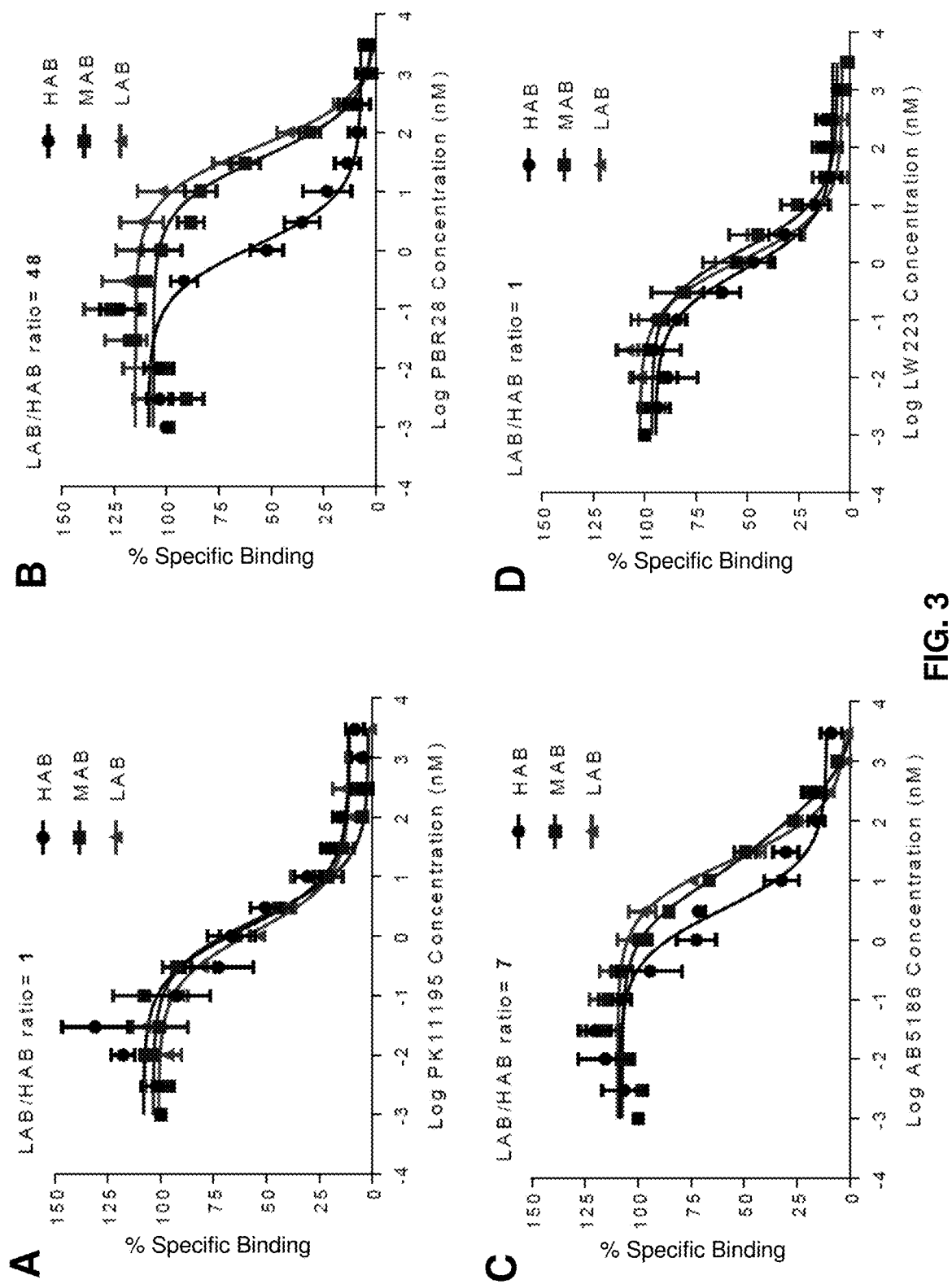
FIG. 3 shows the binding affinity of TSPO ligands in human hearts from high (HAB), mixed (MAB) and low (LAB) affinity binders, where (a) shows the mean PK11195 binding affinity curves plotted using a one-site fitting, HAB n=4, MAB n=5 and LAB n=4; (b) shows the mean PBR28 binding affinity curves plotted using a one-site fitting, HAB n=4, MAB n=5 and LAB n=4; (c) shows the mean AB5186 binding affinity curves plotted using a one-site fitting apart from MAB where a two-site fitting was used, HAB n=4, MAB n=5 and LAB n=4; (d) shows the mean LW223 binding affinity curves plotted using a one-site fitting, HAB n=5, MAB n=5 and LAB n=4: and (e) shows the individually calculated affinity values ($K_i$) for PK11195 against each human sample, which values were also calculated for (f) PBR28, (g) AB5186 and (h) LW223. ns=not significant, **=p≤0.01 using an unpaired t-test for HAB vs. LAB. All results represent the mean±SEM.

As in the brain, PK11195 was also not affected by the genetic polymorphism in the heart, with a LAB:HAB ratio of 1 (FIG. 3(*a*)). PBR28 and AB5186 were affected to a similar degree in the heart vs. the brain, with a ratio of 48 and 7 (FIGS. 3(*b*) and (*c*) respectively). LW223 was not affected by the polymorphism in the heart, with a ratio of 1 (FIG. 3(*d*)). Individually calculated affinity values for all heart samples demonstrated no significant difference between HAB and LAB in PK111195 and LW223 binding studies (FIGS. 3(e) and (h) respectively). In the heart the mean affinity of LW223 was the same as PK11195 at 1.7 nM. In addition, only the MAB group in the AB5186 experiments was suited to a two-site fitting.

Previously, there has been in vivo imaging evidence to suggest that the binding of [11]C-PK11195 was sensitive to the polymorphism in peripheral organs such as the heart and lungs, but not the brain (Kreisl et al.). It has been suggested that PK11195 sensitivity to the polymorphism in the brain cannot be imaged due to a low signal to noise ratio, lower brain uptake compared with the heart and lungs and also the limited subject numbers which are inevitable due to the low prevalence of LAB (Kobayashi et al.). However, with sensitive ex vivo competition binding assays brain uptake levels are less of an issue. In this study differences in affinity between the brain and heart for LW223 (0.6 and 1.2 nM respectively) are demonstrated, unlike PK11195 which was the same (1.2 nM). Improved LW223 affinity in the brain will provide an advantage when targeting neurological inflammation.

Animals and Surgical Procedures

All experiments were conducted in accordance with the local University of Edinburgh animal ethics committee and were authorized by the Home Office under the Animals (Scientific Procedures) Act 1986. 28 adult male Sprague-Dawley rats (357.1±8.1 g and 10.2±0.4 weeks), and 2 C57bl/6 (25.3±3.7 g and 10.1±0.0 weeks) were used for this study, with 2 C57bl/6 (26.0±5.3 g and 13.5±5.7 weeks) used in an additional study. The animals were housed under standard 12 h light:12 h dark conditions with food and water available ad libitum. On the day of the experiment, anesthesia was induced and maintained with 1.5-2.5% isoflurane (50/50 oxygen/nitrous oxide, 1 L/min). For imaging experiments, an intravenous (i.v.) line was established in the femoral vein or tail vein for injection of the radiotracer and the femoral artery was cannulated to allow automated blood sample collection, as previously described (Warnock et al.).

In a separate set of experiments (radiometabolite studies), the femoral artery was cannulated for blood sampling and the radiotracer was administered i.v. via tail vein. Surgical cannulation of femoral vein and artery was performed as follows: polyethylene catheters (PE50) filled with heparinized saline (20 IU/mL) were inserted into the left femoral artery or vein with the help of a stereomicroscope and securely fastened with ligatures (6-0 silk thread). Catheters were held in place with surgical glue. Body temperature was maintained by heated scanner bed or heated mat and monitored by rectal thermometer. Vital signs, including heart rate and respiration rate were monitored continuously during the experiments.

PET Studies

Study Design:

13 PET scans were performed with $^{18}$F-LW223 (mean injected radioactivity of 19.55±2.1 MBq). Scans were acquired following i.v. bolus injection of $^{18}$F-LW223 via tail vein or femoral vein shunt (invasive kinetic modelling experiments with β-probe automatic blood sampler) in rats. Test-retest scans were obtained in three rats following i.v. bolus of the radiotracer, with two weeks interval between test and retest imaging sessions. Blocking studies were carried out by i.v. administration of PK11195 (1 mg/kg) 30 min prior to receiving i.v. $^{18}$F-LW223 in rats. These scans were compared to baseline scans where no PK11195 was used. For displacement studies, rats received i.v. administration of $^{18}$F-LW223 and scanned continuously for 120 min. After 60 min, a single dose of PK11195 (1 mg/kg) was administered. A male and female mouse were initially used to derive the dosimetry estimates for $^{18}$F-LW223 over a 4 h dynamic scan, followed by additional mice in a further study (in a study with a mean injected radioactivity of 10.83±5.6 MBq).

Arterial Input Functions Using the β-Probe Automatic Blood Sampler

A commercially available β-probe system (Twilite2, Swisstrace, Switzerland) was used for the measurement of blood radioactivity as previously described (Warnock et al.). This system allows for whole-blood arterial input function measurements with a temporal resolution of 1 second and without blood loss due to surgically induced arteriovenous shunt. With data acquired in separate studies (radiometabolite experiments), the whole-blood arterial input function measured by the automatic blood sampler was corrected for the plasma-to-whole blood ratio and for metabolism in vivo.

Image Acquisition and Reconstruction

All PET data were acquired using a preclinical PET/CT small animal scanner (nanoPET/CT, Mediso, Hungary). A CT scan (semi-circular full trajectory, maximum field of view, 480 projections, 50 kVp, 300 ms and 1:4 binning) was acquired for attenuation correction. Immediately following radiotracer administration, a 120 minutes emission scan was obtained using 3-dimentional 1:5 mode and re-binned as follows: 18×10 s; 2×30 s; 1×60 s; 2×2 min; 10×5 min; 6×10 min. PET images were reconstructed using Mediso's iterative Tera-Tomo 3D reconstruction algorithm and the following settings: 4 iterations, 6 subsets, full detector model, low regularization, spike filter on, voxel size 0.4 mm and 400-600 keV energy window. PET data were corrected for randoms, scatter and attenuation.

Image Processing and Data Analysis Reconstructed scans were imported into PMOD 3.8 software (PMOD Technologies, Switzerland). Volumes of interest (VOIs) were manually drawn around organs of interest. Time-activity curves (TACs) were generated and standardized uptake values (SUVs) calculated as concentration in the VOI divided by injected dose divided by animal weight. Kinetic modelling was performed using compartmental analysis (1-Tissue (1T) and 2-Tissue (2T) models) and graphical analysis (Logan plot and Ichise multivariate analysis) to estimate the volume of distribution ($V_T$) in different tissues (Innis et al.; Logan; and Ichise et al.). Model fitting performance was evaluated using the Akaike information criterion (AIC) and the model selection criterion (MSC), where the preferred model had the lowest AIC and highest MSC. The selected identifiability criterion was the percentage standard error (% SE) of $V_T$ estimates. Kinetic modeling was also performed using graphical analysis to estimate the distribution volume ratio (DVR) in tissue regions and organs where the reference region VOI was the blood pool VOI in the left ventricle (Logan et al.).

Test-retest reproducibility of DVR was calculated as the absolute of the average measurements divided by standard deviation: ABS (average test/retest)/SD (test/retest).

Dosimetry

Reconstructed whole-body PET scans were imported into PMOD 3.8 software (PMOD Technologies, Switzerland) and VOIs were drawn around organs that displayed higher radioactivity concentration than background, i.e. source organs. The following organs were identified as source organs: brain, heart, lungs, gallbladder, liver, gut, adrenals, kidneys and bladder. A whole-body VOI was drawn around the animal body and was used for quantification of whole-body remainder activity as whole-body activity minus source organs activity. At each time point, the measured activity of the source organs was expressed as the percent injected dose (% ID).

The residence time T, defined as the ratio of accumulated activity in the target organ (A) and injected activity ($A_0$); $\tau = \overline{A}/A_0$, was calculated as the area under the curve of the tissue time-activity curve normalized to % ID from time zero to infinity. The trapezoidal method was used for estimating T and after the last measured time point, it was assumed that the radiotracer underwent only physical decay with no biological elimination from the source organ. Calculated T were normalized for differences in mouse and human organ weights as a percentage of total body weight (based on data known from Khanuja et al.; Bielohuby et al.; Stabin et al.; Hindorf et al.; and Hui et al.), and entered into OLINDA/EXM 1.0 software, which was used to estimate organ doses and effective doses according to the male or female model implemented in OLINDA/EXM 1.0.

Comments

Figure 4:
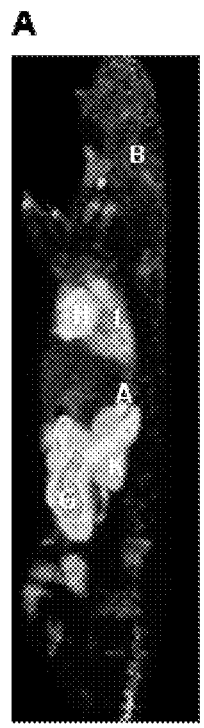
FIG. 4 shows the $^{18}$F-LW223 kinetic and metabolic profile in vivo, where (a) is the maximum intensity projection image of a rat and (B) is the projection image of a mouse, showing the distribution of $^{18}$F-LW223 under basal conditions. B=brain, H=heart, L=lungs, GB=gall bladder (mouse only), A=adrenal gland, K=kidney and G=gut; (c) and (d) are rat and mouse $^{18}$F-LW223 time activity curves respectively; (e) shows the rat blood kinetics of $^{18}$F-LW223 showing the % of parent compound within plasma where the results represent the mean±SEM, n=3 per time point; and (f) shows the distribution volume ($V_t$) values in organs calculated by 2-tissue (2T), Logan (t*=30) and multivariate (M1, t*=30) modelling, mean±SD, n=3.
Figure 4:
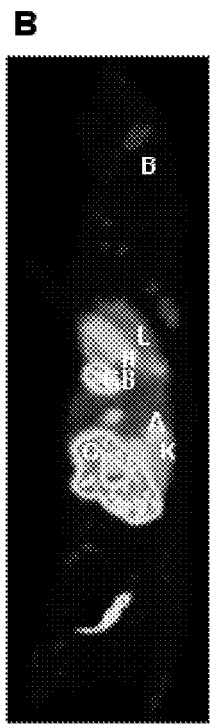
Figure 4:
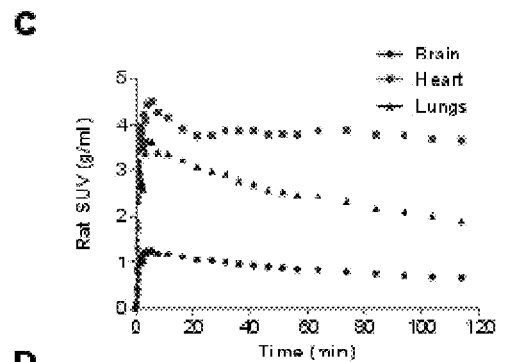
Figure 4:
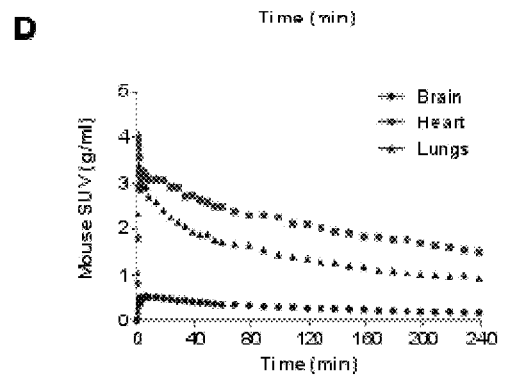
Figure 4:
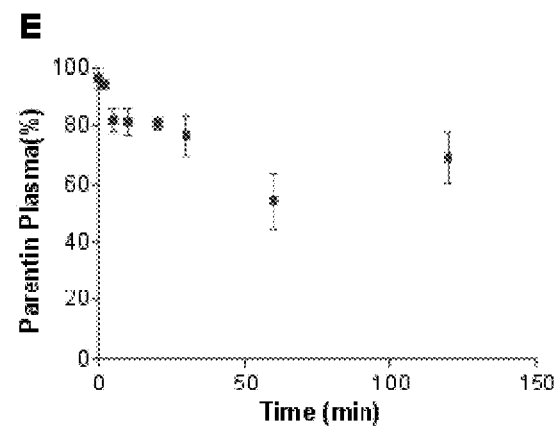
Figure 4:
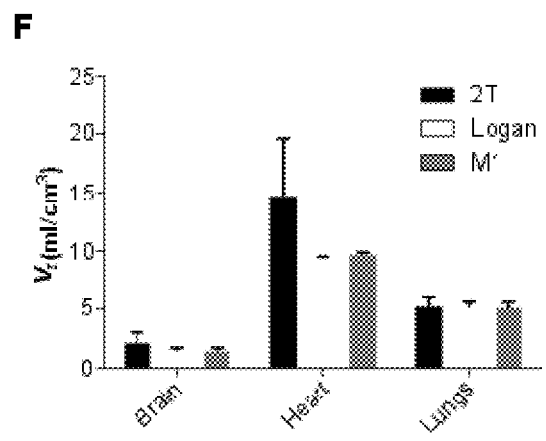

In mice and rats, following intravenous bolus injection, $^{18}$F-LW223 rapidly distributed to TSPO expressing tissues, including brain, heart, lungs and adrenals (see FIGS. 4(*a*) and (*b*)); and was eliminated via both the urinary and hepatobiliary excretion routes. Post-peak uptake, elimination of the radiotracer was faster in brain and lungs compared with heart (see FIGS. 4(*c*) and (*d*)).

Radiometabolism of $^{18}$F-LW223 in rat arterial blood was slow with approximately 70% parent at 120 minutes post-injection (FIG. 4(*e*)). Less than 10% radioactive metabolites were measured in the brain, heart and lungs at 60 and 120 minutes post-administration ( ). The measured parent free fraction in plasma was 38.5±7.0% (mean±SEM, n=XX).

$^{18}$F-LW223 kinetics in vivo was reversible and better fitted/described by the 2-tissue compartmental model, as well as, graphical Logan plot (t*=30 minutes) and Ichise multivariate analysis (t*=30 minutes), (see FIG. 4(*f*)). Graphical methods were preferred over compartmental models (lower % standard error, lower Akaike selection criteria and higher model selection criteria). Measured $V_T$s in brain, heart and lungs were 1.46 0.16, 9.48±0.03 and 5.13±0.29 respectively (Logan modelling, mean±SEM, n=3), respectively. Distribution volume ratios (DVR) relative to blood pool in brain, heart and lungs were 0.53±0.06, 2.96±0.14 and 1.84±0.13 (mean±SEM, n=3), respectively. The test-retest analysis showed good agreement of measurements and an inter-subject variability of 16% in brain, 2% in heart and 15% in the lungs when using DVR as the outcome measure.

Figure 5:
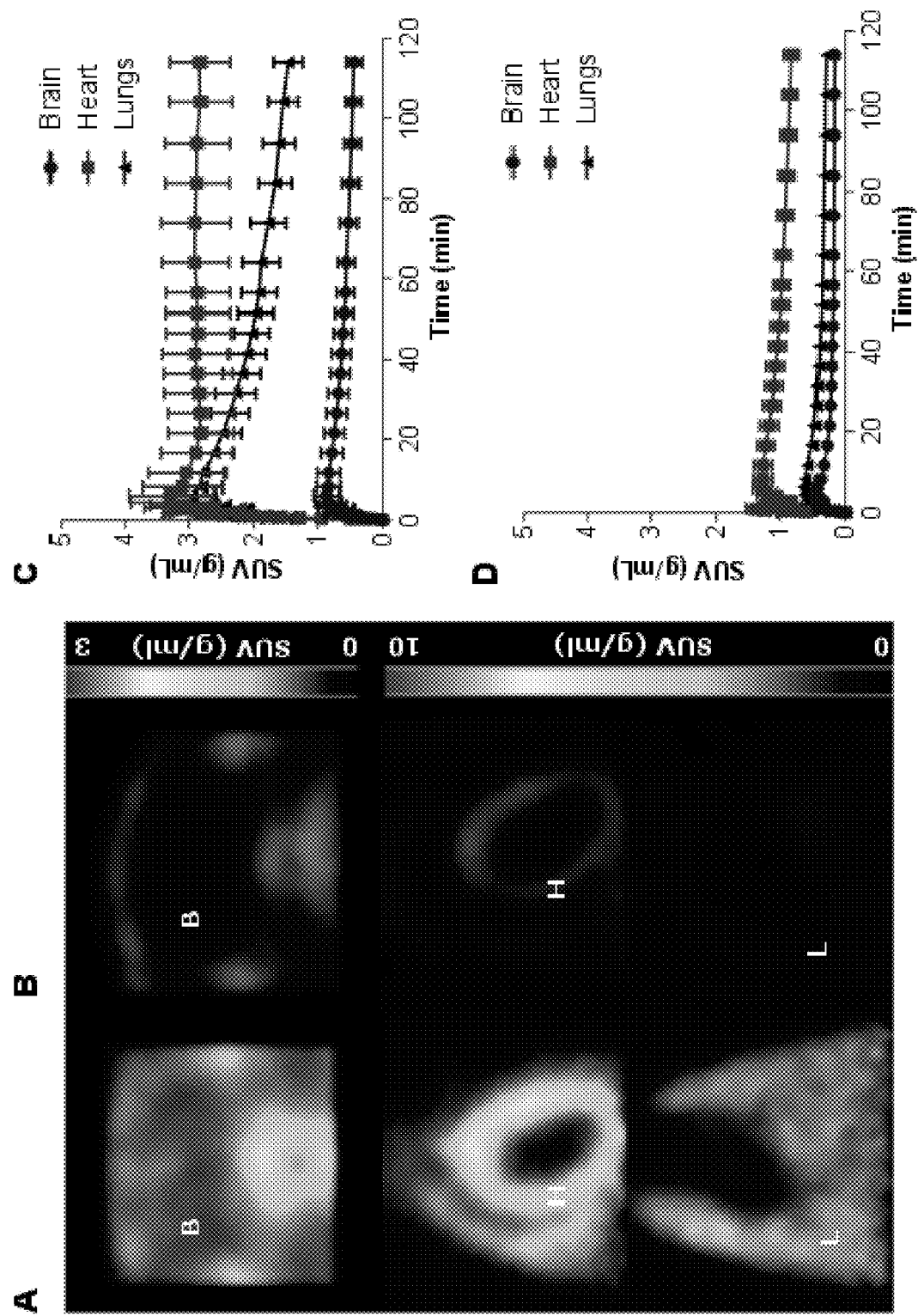
FIG. 5 shows $^{18}$F-LW223 binding to TSPO in vivo, where (a) shows the SUV sum images showing $^{18}$F-LW223 uptake in the brain (B), heart (H) and lungs (L); (b) shows the SUV sum images of $^{18}$F-LW223 uptake administered following blockade with PK11195 (1 mg/kg). All images are averaged (60-120 min.) and have had a Gaussian filter applied (1×1× 1); and (c) shows the $^{18}$F-LW223 time activity curves for the major source organs at baseline and (d) following PK11195 blockade. The results represent the mean±SEM, n=3.
Figure 8:
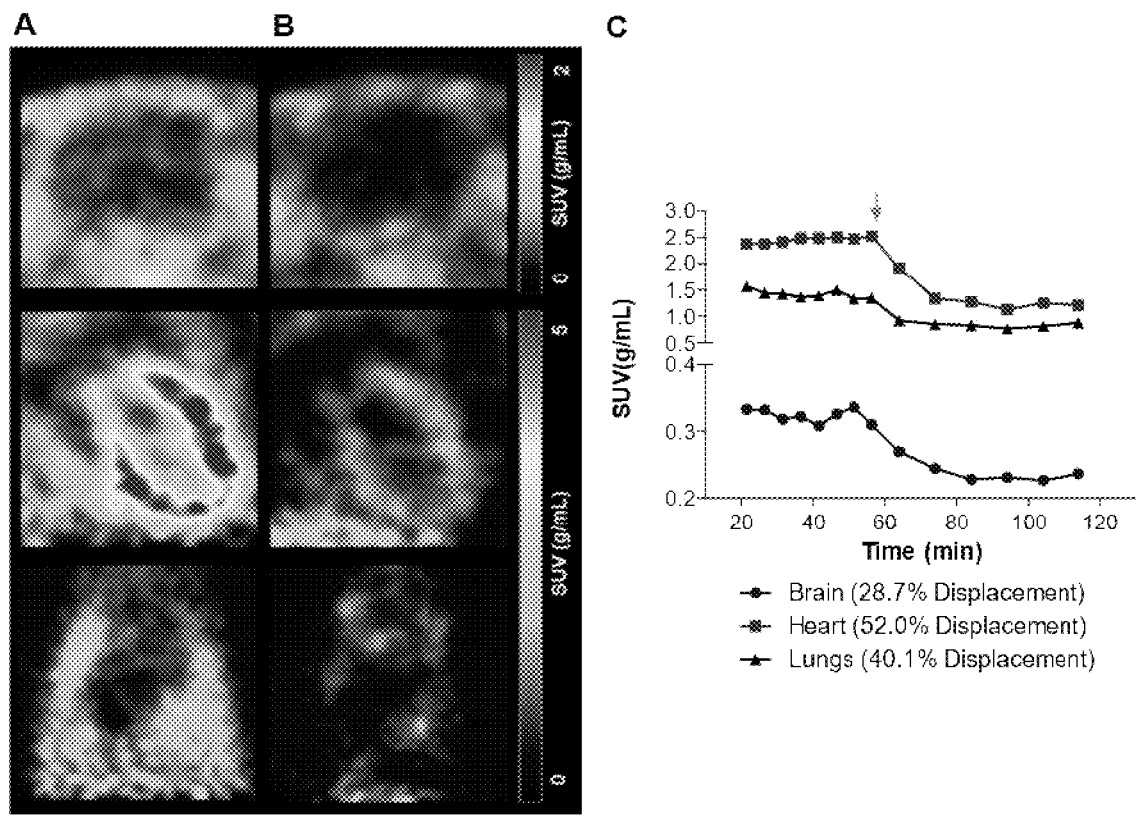
FIG. 8 shows the in vivo displacement of $^{18}$F-LW223 using PK11195, where (a) is the SUV sum image of $^{18}$F-LW223 uptake before displacement; (b) is the SUV sum image after displacement with PK11195 (1 mg/kg), where the baseline images are averaged before PK11195 administration (45-60 min.) and displacement images are averaged after (95-120 min.). All images have had a Gaussian filter applied (1×1×1); and (c) is the time activity curve of $^{18}$F-LW223 before and after (green arrow) PK11195 challenge.

Administration of PK11195 prior to $^{18}$F-LW223 injection demonstrated target engagement in vivo (see FIG. 5). There was a 64-81% reduction on the SUV values measured post-blocking compared with baseline scans. Measured $V_T$s post-blocking in brain, heart and lungs were 1.29 0.12, 6.19±0.38 and 2.27±0.07 (mean±SEM, n=3), respectively. This corresponds to 12%, 35% and 56% reduction of radiotracer binding for brain, heart and lungs, respectively. The same dosage of PK11195 was able to displace $^{18}$F-LW223 from target sites at equilibrium time point by 29%, 52% and 40% in brain, heart and lungs respectively (see FIG. 8). Pharmacokinetic/Pharmacodynamic studies with PK11195 in rats at 1 hour showed that exposure levels in brain were 11.01±1.99 ng/mL versus 29.31±3.93 ng/mL and 38.86±2.24 ng/mL (mean±SEM, n=3) in heart and lungs, respectively. This is in agreement with measured blocking and displacement in PET experiments, and % target engagement differences in brain and peripheral organs agree with $K_i$ measured for LW223 and PK11195 in vitro.

Figure 9:
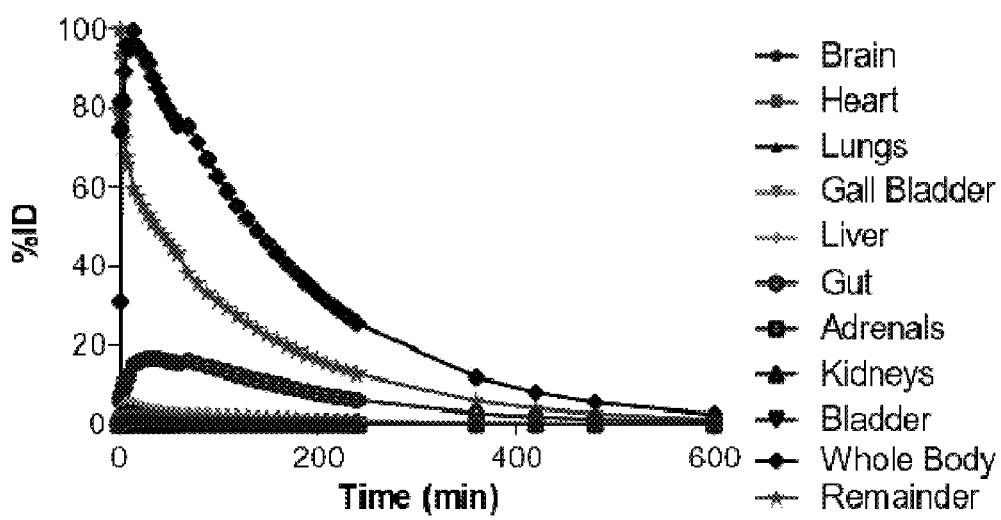
FIG. 9 shows the $^{18}$F-LW223 time activity curves of source organs in mice, where (a) is the time activity curve of $^{18}$F-LW223 across all sites with uptake greater than background in a male mouse; and (b) is the time activity curve of $^{18}$F-LW223 across all sites with uptake greater than background in a female mouse. PET raw data was reconstructed using filtered-back projection without decay correction.
Figure 9:
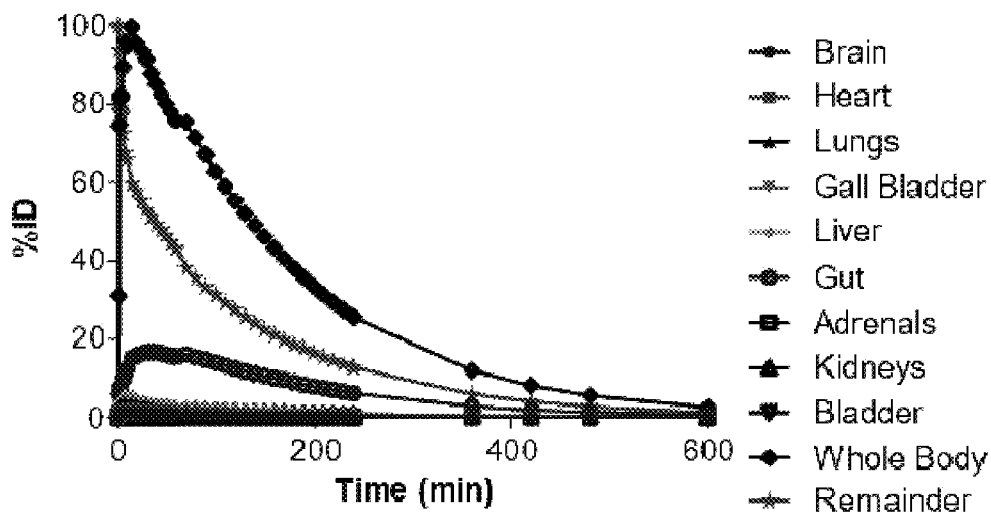

Whole-body effective time-activity curves showed the highest peak % injected dose was in the large intestine followed by the liver, lungs, Kidneys, heart, brain, gall bladder, bladder and adrenals (see FIG. 9). Dosimetry estimates using normalized tau values and the male and female adult human phantom showed the critical organ was the adrenal gland. The whole-body effective dose was estimated to be 15.3 μSv/MBq and 18.4 μSv/MBq for the male and female phantom, respectively (Table 1).

Following additional work with further mice, the critical organ was found to be the lower intestinal wall. The whole-body effective dose was estimated to be 20.5 μSv/MBq and 23.7 μSv/MBq for the male and female phantom, respectively (Table 2).

TABLE 1

Estimated Absorbed Dose in Selected Target Organs
Estimated Absorbed Dose (mGy/MBq)

| Target Organ | Male | Female |
| --- | --- | --- |
| Adrenals | 3.72E−02 | 4.38E−02 |
| Brain | 7.01E−03 | 8.38E−03 |
| Breasts | 9.21E−03 | 1.16E−02 |
| Gallbladder Wall | 2.42E−02 | 2.80E−02 |
| LLI Wall | 1.28E−02 | 1.61E−02 |
| Small Intestine | 3.38E−02 | 3.97E−02 |
| Stomach Wall | 1.23E−02 | 1.54E−02 |
| ULI Wall | 1.52E−02 | 1.89E−02 |
| Heart Wall | 3.07E−02 | 3.96E−02 |
| Kidneys | 2.38E−02 | 2.67E−02 |
| Liver | 1.56E−02 | 2.04E−02 |
| Lungs | 3.57E−02 | 4.52E−02 |
| Muscle | 1.02E−02 | 1.27E−02 |
| Ovaries | 1.40E−02 | 1.71E−02 |
| Pancreas | 1.35E−02 | 1.68E−02 |
| Red Marrow | 1.02E−02 | 1.25E−02 |
| Osteogenic Cells | 1.54E−02 | 2.01E−02 |
| Skin | 7.82E−03 | 9.71E−03 |
| Spleen | 1.19E−02 | 1.51E−02 |
| Testes | 9.46E−03 | — |
| Thymus | 1.16E−02 | 1.47E−02 |
| Thyroid | 1.02E−02 | 1.19E−02 |
| Urinary Bladder Wall | 1.37E−02 | 1.51E−02 |
| Uterus | — | 1.67E−02 |
| Total Body | 1.12E−02 | 1.40E−02 |
| Effective Dose (mSv/MBq) | 1.53E−02 | 1.84E−02 |

TABLE 2

Estimated Absorbed Dose in Selected Target Organs
Estimated Absorbed Dose (mGy/MBq)

| Target Organ | Male | Female |
| --- | --- | --- |
| Adrenals | 2.22E−02 | 3.54E−02 |
| Brain | 5.89E−03 | 5.49E−03 |
| Breasts | 7.18E−03 | 8.51E−03 |
| Gallbladder Wall | 2.01E−02 | 2.40E−02 |
| LLI Wall | 7.82E−02 | 8.94E−02 |
| Small Intestine | 1.11E−02 | 1.29E−02 |
| Stomach Wall | 9.42E−03 | 1.14E−02 |
| ULI Wall | 9.96E−03 | 1.24E−02 |
| Heart Wall | 2.03E−02 | 1.80E−02 |
| Kidneys | 1.57E−02 | 1.48E−02 |
| Liver | 1.30E−02 | 1.88E−02 |
| Lungs | 3.10E−02 | 3.10E−02 |
| Muscle | 8.04E−03 | 9.70E−03 |
| Ovaries | — | 1.63E−02 |
| Pancreas | 1.03E−02 | 1.25E−02 |
| Red Marrow | 8.22E−03 | 9.72E−03 |
| Osteogenic Cells | 1.20E−02 | 1.52E−02 |
| Skin | 6.09E−03 | 7.33E−03 |
| Spleen | 9.11E−03 | 1.10E−02 |
| Testes | 7.70E−03 | — |

TABLE 2-continued

Estimated Absorbed Dose in Selected Target Organs
Estimated Absorbed Dose (mGy/MBq)

| Target Organ | Male | Female |
|---|---|---|
| Thymus | 8.97E−03 | 1.06E−02 |
| Thyroid | 7.90E−03 | 8.89E−03 |
| Urinary Bladder Wall | 1.16E−02 | 1.49E−02 |
| Uterus | — | 1.28E−02 |
| Total Body | 8.85E−03 | 1.06E−02 |
| Effective Dose (mSv/MBq) | 2.05E−02 | 2.37E−02 |

Radiometabolite and Arterial Blood Processing and Analysis

Arterial blood samples were collected at 2, 5, 10, 20, 30, 60 and 120 minutes post-radiotracer administration (69.8±9.2 MBq, n=17 rats). All blood samples were 1 mL each and manually collected from different animals to generate a population curve, in order to respect total blood volume limits for terminal arterial blood collections in rats. Following blood collection, all samples were kept on ice until analyzed. Radioactivity in whole blood and plasma was assessed using a well-type γ-counter using a 400-1400 keV window (Perkin Elmer Wizzard2, USA). Plasma samples (400 µL) were processed by acetonitrile denaturation and analyzed by HPLC (Ultimate2000, ThermoFisher, UK) on a Luna C18(2) column (Luna C18(2), 10×250 mm, 10 µm, Phenomenex, UK) with a mobile phase of acetonitrile/water 70/30 at a flow rate of 4 mL/min to estimate the parent fraction. The plasma protein binding free fraction (f) was determined using ultrafiltration units (Centrifree® 30K, Millipore, UK).

$^{18}$F-LW223 Human Autoradiography

Paraffin embedded human deep brain stoke tissue and diseased coronary tissue sections at 1-2 levels were dewaxed, rehydrated and incubated in buffer (50 mM Tris-Base, pH 7.4) for 30 min prior to incubation with 2 MBq/mL of $^{18}$F-LW223 (total binding group) in the presence or absence of either PK11195 (30 µM in stoke tissue and 10 µM in coronary tissue) or LW223 (10 µM, non-specific binding group). Slides were washed twice with buffer before being air dried and exposed to a Fujifilm BAS-IP MS 2040 phosphor screen (Fujifilm, Japan). Phosphor screens were imaged on a Fujifilm FLA5100 imaging plate reader (Fujifilm, Japan). Global regions of interest were drawn around whole tissue sections to calculate % SB. To calculate target:non-target ratios, regional sampling analysis was used within the same tissue in the highest and lowest uptake areas.

Comments

Figure 6:
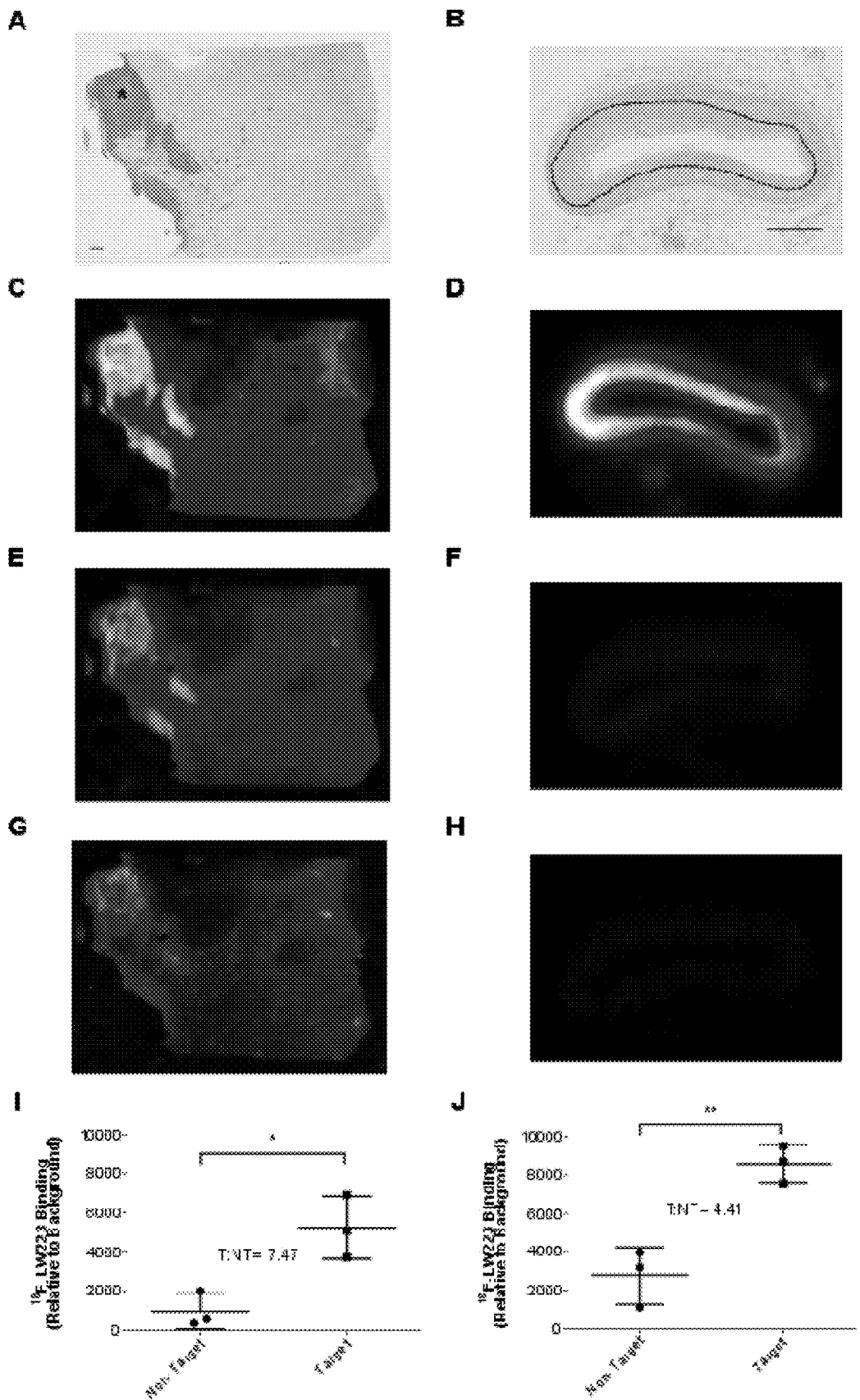
FIG. 6 shows $^{18}$F-LW223 binding to human tissue, and reveals regional uptake at sites of pathology, where (a) shows H&E staining of brain tissue from an individual who suffered a haemorrhagic stroke, *=haemorrhage area. Scale bar=1,000 μM; (b) shows a histological example (H&E) of a diseased coronary vessel exhibiting pathological neointimal remodelling. The dotted line represents the boundary between original medial layer and neointima. Scale bar=1, 000 μM; (c) is the autoradiography of $^{18}$F-LW223 binding to invading inflammatory cells within the stroke tissue; (d) is the autoradiography of $^{18}$F-LW223 binding to inflammatory cells within the neointima of diseased coronary vessels; (e) shows the blockage of $^{18}$F-LW223 binding using PK11195 in stoke and (f) diseased coronary tissue: (g) shows the blockage of $^{18}$F-LW223 binding using LW223 in stroke and (h) diseased coronary vessels: (i) shows the quantification of $^{18}$F-LW223 binding in regions of high and low uptake together with the target to non-target ratio in stoke and (j) diseased coronary tissue. The results represent the mean±SEM, n=3, *=p<0.05, **=p≤0.01 using a paired t-test for target vs. non-target.
Figure 10:
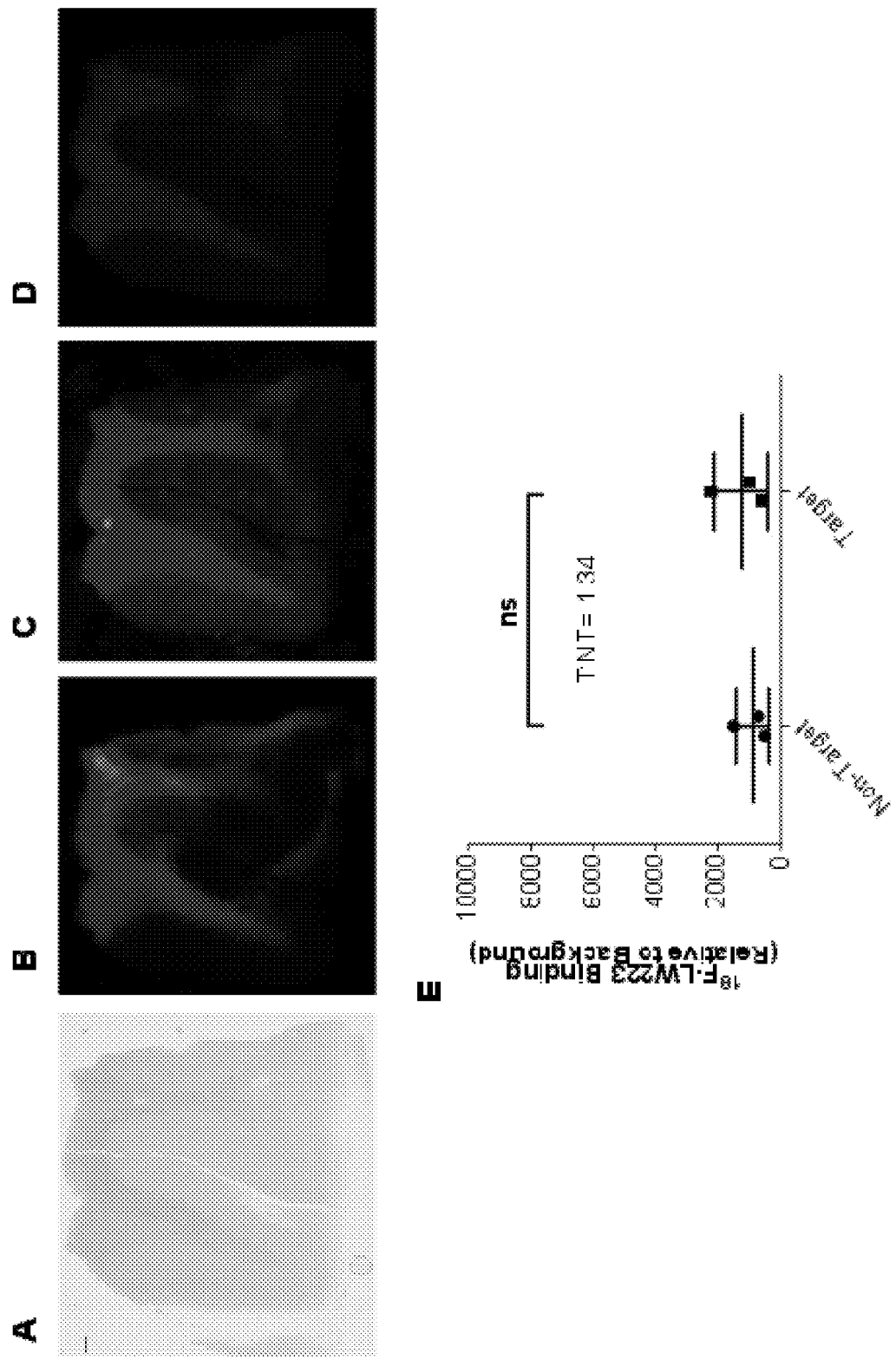
FIG. 10 shows the binding of $^{18}$F-LW223 in healthy human brain tissue, where (a) is the H&E stain of healthy brain; (b) is the autoradiography of $^{18}$F-LW223 binding in healthy brain; (c) is the blockage of $^{18}$F-LW223 binding using PK11195; (d) is the blockage of $^{18}$F-LW223 binding using LW223; and (e) is the quantification of $^{18}$F-LW223 binding in regions of grey matter together with their target to non-target ratio. The results represent the mean S.E.M, n=3, ns=not significant using a paired t-test for target vs. non-target. Scale bar=1,000 μM.

Autoradiography was used to image binding of $^{18}$F-LW223 to ex vivo human diseased tissue. Histological staining of tissue revealed areas of hemorrhage containing migrating inflammatory cells in deep brain stroke specimens (see FIG. 6(a)). In diseased coronary vessels from sudden cardiac death patients, there were clear areas of pathological remodeling (e.g. neointimal hyperplasia) which contained infiltrating inflammatory cells (FIG. 6(b)). The binding of $^{18}$F-LW223 in stoke was highest in the hemorrhagic region, with some uptake in remote regions (FIG. 6(c)). In diseased coronary vessels, binding of $^{18}$F-LW223 was highest in areas pathological remodeling (FIG. 6(d)). The binding of $^{18}$F-LW223 could not be sufficiently blocked using PK11195 in deep brain tissue samples (FIG. 6(e)), whereas in the coronaries a % specific binding (% SB) of 75.3±3.2 was achieved (FIG. 6(f)). Blocking with LW223 in stoke samples achieved 42.5±7.0% SB (FIG. 6(g)) and in coronaries 88.1±3.4% SB (FIG. 6(h)). Importantly, a high target:non-target ratio was achieved in both stoke (7.5) and diseased coronary (4.5) tissue (FIGS. 6(i) and (j)). In comparison with healthy human brain, there were no regions of high uptake other than some non-specific binding in white matter (see FIG. 10).

General Statistical Analysis

Graphpad Prism version 6 (GraphPad Software Inc., USA) was used for all fitting, statistical analysis and production of graphs. In competition binding assays and saturation assays, outliers within experimental triplicates were removed using a Grubbs test with an alpha of 0.2. Unpaired and paired t-tests were used in this study for comparison between two groups, as indicated within the relevant figure legends, with a p<0.05 considered statistically significant. All error bars represent the standard error mean (SEM), unless otherwise indicated in the figures or tables legends.

Comments

Recently, a study was published which for the first time detailed the crystalline structure of TSPO with and without the Thr$^{148}$ polymorphism (Li et al.). In this study the authors elegantly demonstrated that the binding of PK11195 stabilizes the binding pocket, while the polymorphism has a large impact on the cholesterol binding site. This evidence suggests that ligands which engage with the cholesterol site may display a greater sensitivity to the polymorphism. Though various binding studies, it is known that the TSPO binding site has three main binding pockets; the benzodiazepine site, the isoquinoline site and the cholesterol site (Li et al.; Lin et al.; and Luus et al.). As LW223 is insensitive to the polymorphism in the brain and heart and is structurally similar to PK11195, we speculate that LW223 is targeting the isoquinoline site rather than the cholesterol. However, the differences in overall affinity values for LW223 in the brain and heart suggests an organ specific conformational change in the TSPO isoquinoline binding pocket across different across sites.

As well as being the first fluorinated TSPO ligand to be insensitive to the rs6971 polymorphism, $^{18}$F-LW223 is also unique in that it exists as a rotamer. This was evident by the presence of two peaks on the HPLC, and confirmed by chiral HPLC. This unusual characteristic may be behind the excellent kinetic and metabolic properties of $^{18}$F-LW223, which display a profile which is similar to an infusion administration in spite of being administered by IV bolus. Another unique aspect of $^{18}$F-LW223 was the high plasma free fraction, which was 38.5%, in comparison to $^{11}$C-PK11195 which has a free fraction of 1-6% in humans (Owen et al.; Endres et al.) Clearly, further investigation is required to determine this unique aspect and its contribution to the favorable kinetic and metabolic profiles. While these characteristics do not hinder the translation of $^{18}$F-LW223 into the clinic, other criteria must still be met. First off, a toxicology package is yet to be carried out in order to determine the safety of this radiotracer. It should be noted that no negative effects were apparent following administration of $^{18}$F-LW223 in vivo. Secondly, while the dosimetry estimates presented within this study do not suggest any radiological safety issues.

The limitations of this study are similar to those which are faced by most studies developing novel TSPO radiotracers. First of all, the prevalence of LAB in this study was around 14%, which while higher than the prevalence reported in other studies (Fujita et al.), limits the available samples for testing. However, this study found that the LAB:HAB ratio for PK11195 and PBR28 in the brain was similar to that which was previously reported (Owen et al. *J. Cereb. Blood*

Flow Metab. 2012; Owen et al.; Owen et al. *J. Cereb. Blood Flow Metab.*), with PBR28 and AB5186 reaching statistically significant differences between LAB and HAB. Some controversy has also arisen in the field where in vitro binding study results have not mirrored those in vivo. The TSPO radiotracer [11]C-ER176 displayed a LAB:HAB ratio of 1.3 in vitro (Zanotti-Fregonara et al.); however in later in vivo studies it was found to have a ratio of around 3 (Ikawa et al.). It was however reported that even with this minor effect of the polymorphism, [11]C-ER176 still had the ability to image LAB, an achievement which is not possible with other ligands. If the same phenomenon was to hold true for [18]F-LW223, this radiotracer still benefits from being fluorinated, bringing with it wider clinical use. One of the finial limitations of this study was that it was carried out in rodents, which usually display faster kinetics and metabolism than non-human primates and humans. However, even with this caveat, the kinetic and metabolic profiles of [18]F-LW223 in this study suggest that these aspects will not be an issue when translated.

Due to the role of inflammatory, phagocytic cells such as macrophages and microglia in a range of pathologies, the development of a successful TSPO imaging approach has significant potential. In this study we demonstrate that ex-vivo uptake of [18]F-LW223 is evident in areas of pathological, inflammatory driven events. Previously, [11]C-PK11195 has been successfully used to demonstrate increased inflammation in neurological diseases, in spite of its limitations. For example, increased [11]C-PK11195 uptake has been demonstrated in patients with Alzheimer's disease and progressive supranuclear palsy compared with controls (Calsolaro et al.). Regions of increased uptake were associated with established neuropathological distribution patterns in both diseases, and correlated negatively with episodic memory in Alzheimer's disease, and positively disease severity in progressive supranuclear palsy. [11]C-PK11195 has also been successfully used to investigate atherosclerotic plaque inflammation. In an ex vivo study, [11]C-PK11195 binding was found to correlate with macrophage rich regions (Bird et al.). In an in vivo clinical study, [11]C-PK11195 uptake within plaques was able to distinguish between recently symptomatic and asymptomatic lesions (Gaemperli et al.). These positive clinical studies, in addition to the emerging role of TSPO as a therapeutic target (Schalle et al.; and Paradis et al.), highlight the potential which can be gained from a successful TSPO radiotracer as a research tool, diagnostic agent and therapeutic companion imaging agent.

In conclusion, the insensitivity of [18]F-LW223 to the rs6971 genetic polymorphism, longer half-life of the radiolabel and favorable kinetics make this novel TSPO radiotracer a promising breakthrough in the field of TSPO imaging, warranting further translation to the clinic.

Additional Experimental and Results

[13]F-LW223 Binding in Rat Model of Myocardial Infarction

Figure 11:
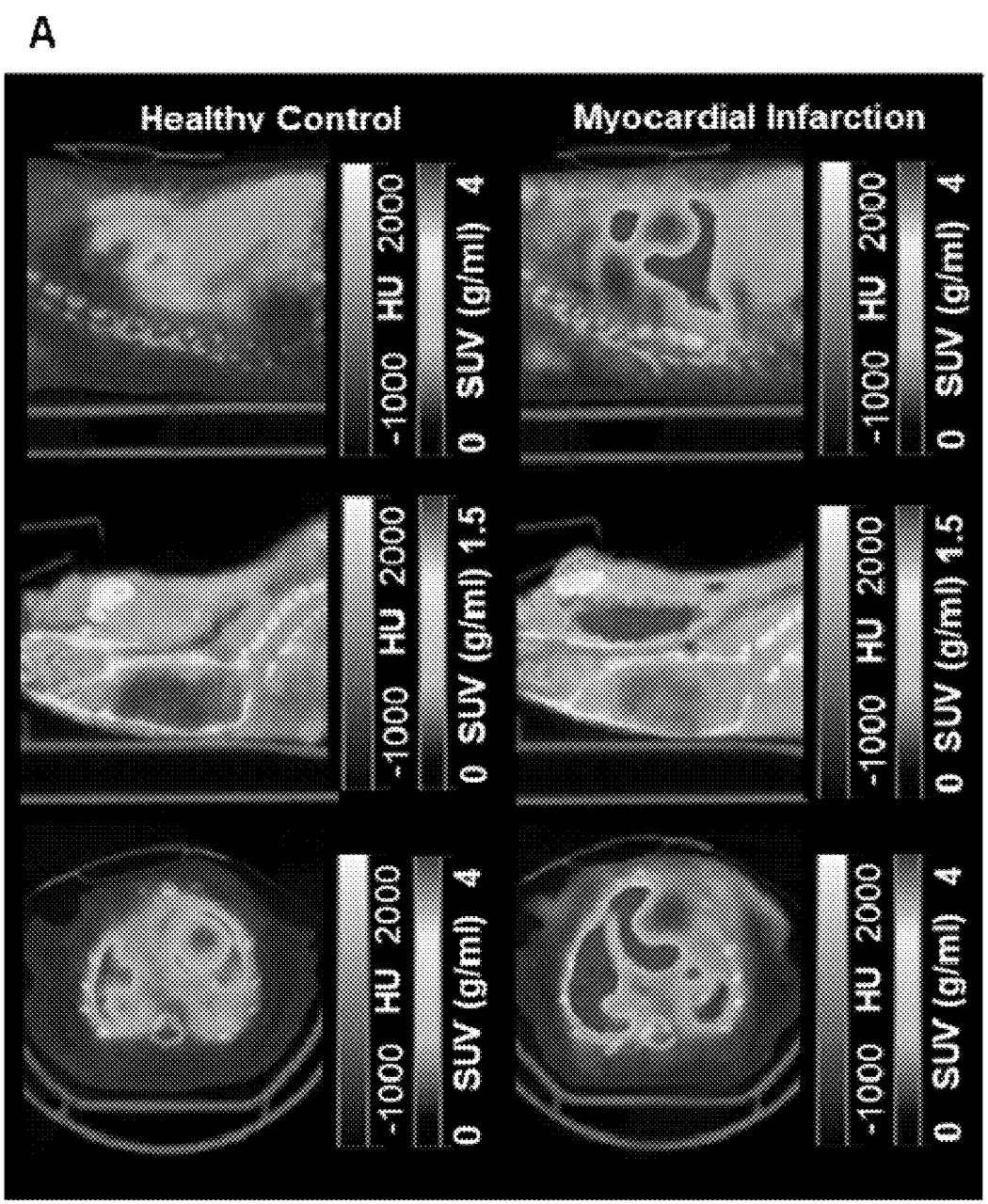
FIG. 11 shows the results of an uptake study of $^{18}$F-LW223 in rats with induced myocardial infarction, demonstrating that myocardial infarction leads to increased $^{18}$F-LW223 uptake in the heart, brain and lungs, where (A) are example $^{18}$F-LW223 SUV images of the heart (top), brain (middle) and lungs (bottom) in healthy (left) and myocardial infarction rats (right) 7 days post-injury; (B) shonws SUV time activity curves in the heart, brain and lungs for healthy (red circles) and myocardial infarction rat (blue squares); and (C) shows SUVr, relative to blood pool, time activity curves the heart, brain and lungs for healthy (red circles) and myocardial infarction rat (blue squares). Mean±SEM, n=5-6.

Rats underwent permanent of ligation of the left anterior descending coronary artery to induce myocardial infarction and after 7 days were imaged using [18]F-LW223 PET/CT (see FIG. 11). Naive rats were used as a healthy control for comparison. Quantification of the standard uptake value (SUV) relative to the blood pool (measured in the left ventricle) demonstrated an increase in [18]F-LW223 binding across the heart, brain and lungs. This indicates a myocardial infarction mediated increase in expression of TSPO within these organs which may also be interpreted as increased systemic inflammation.

REFERENCES

All documents mentioned in this specification are incorporated herein by reference in their entirety.

Alam et al. *Med. Mol. Imaging* (2010). 51, 283-296 (2017).
Bielohuby et al. *Am. J. Physiol. Metab.* 293, E139-E146 (2007).
Bird et al. *Atherosclerosis* 210, 388-391 (2010).
Blair et al. *Med. Chem. Commun.* 4, 1461-1466 (2013).
Blair et al. *Chem. Sci.* 6, 4772-4777 (2015).
Calsolaro et al. *Alzheimer's Dement.* 11, P 792 (2015).
Cappelli et al. *J. Med. Chem.* 40, 2910-2921 (1997).
Cappelli et al. *J. Med. Lett.* 14, 4055-4066 (2006)
Charbonneau et al. *Circulation* 73, 476-483 (1986).
Chauveau et al. *Eur. J. Nucl. Med. Mol. Imaging* 35, 2304-2319 (2008).
Cosenza-Nashat et al. *Neuropathol. Appl. Neurobiol.* 35, 306-328 (2009).
Dupont et al. *Int. J. Mol. Sci.* 18, 785 (2017).
Endres et al. *J. Nucl. Chem.* 50, 1276-82 (2009).
Fairweather et al. *J. Cardiovasc. Trans. Res.* 7, 192-202 (2014).
Fujimura et al. *Atherosclerosis* 201, 108-111 (2008).
Fujita et al. *EJNMMI Res.* 7 (2017), doi:10.1186/s13550-017-0334-8.
Gaemperli et al. *Eur. Heart J.* 33, 1902-1910 (2012).
Hindorf et al. *J. Nucl. Med.* 45, 1960-5 (2004).
Hui et al. *Cancer* 73, 951-957 (1994).
Ichise et al. *J. Cereb. Blood Flow Metab.* 22, 1271-1281 (2002).
Ikawa et al. *J. Nucl. Med.* (2016), doi:10.2967/jnumed.116.178996.
Innis et al. *J. Cereb. Blood Flow Metab.* 27, 1533-1539 (2007).
Khanuja et al. *Genet. Commun.* 92, 7729-7733 (1995).
Kobayashi et al. *J. Cereb. Blood Flow Metab.* 38, 393-403 (2018).
Kreisl et al. *Neuroimage* 49, 2924-2932 (2010).
Lacapère *Steroids* 68, 569-585 (2003).
Li et al. *Clin. Exp. Pharmacol. Physiol.* 42, 1068-1074 (2015).
Li et al. *Science* 347, 555-558 (2015).
Lin et al. *Genomics* 18, 643-50 (1993).
Logan et al. *J. Cereb. Blood Flow Metab.* 16, 834-840 (1996).
Logan *Nucl. Med. Biol.* 27, 661-670 (2000).
Luus et al. *J. Label. Compd. Radiopharm.* 53, 501-510 (2010).
Owen et al. *J. Cereb. Blood Flow Metab.* 30, 1608-18 (2010).
Owen et al. *J. Cereb. Blood Flow Metab.* 32, 1-5 (2012).
Owen et al. *J. Nucl. Med.* 52, 24-32 (2011).
Papadopoulos et al. *Trends Pharmacol. Sci.* 27, 402-409 (2006).
Paradis et al. *Cardiovasc. Res.* 98, 420-427 (2013).
Schalle et al. *J. Pharmacol. Exp. Ther.* 333, 696-706 (2010).
Stabin et al. *J. Nucl. Med.* 47, 655-9 (2006).
Stevenson et al. *Bioorg. Med. Chem. Lett.* 20, 954-957 (2010).
Thackeray et al. *J. Am. Coll. Cardiol.* 71, 263-275 (2018).
Warnock et al. *EJNMMI Res.* 1, 1-11 (2011).
Wilms et al. *Neurobiol. Dis.* 14, 417-424 (2003).
WO 02/26713
Zanotti-Fregonara et al. *ACS Chem. Neurosci.* (2014), doi: 10.1021/cn500138n.

The invention claimed is:

1. A compound of formula (I):

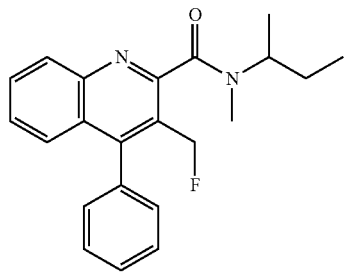

(I)

and salts, solvates and radiolabelled forms thereof.

2. The compound of claim 1 having the structure:

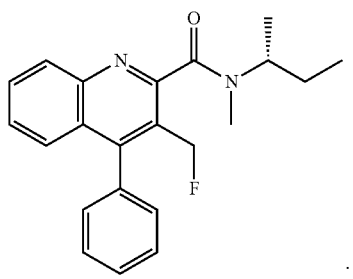 [SMILES: CC[C@@H](C)N(C)C(=O)c1nc2ccccc2c(-c2ccccc2)c1CF]

3. The compound of claim 1 which is a compound of formula (II):

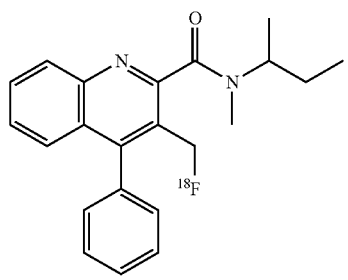

(II)

and salts and solvates thereof.

4. The compound of claim 3 having the structure:

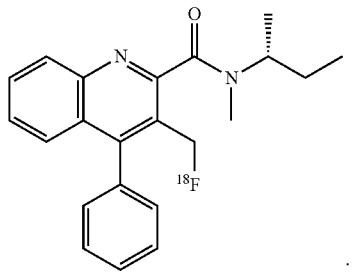

5. A complex comprising a compound according to claim 1 non-covalently bound to TSPO.

6. A method of detecting TSPO, the method comprising the steps of contacting a compound of formula (I) according to claim 1 with TSPO, forming a complex comprising the compound non-covalently bound to TSPO, and detecting the compound.

7. The method of claim 6, wherein the compound of formula (I) is administered to a subject.

8. The method of claim 6, wherein the compound of formula (I) is radiolabelled, and the compound is detected by positron emission tomography.

9. The method of claim 6, wherein the compound of formula (I) is a compound having the structure:

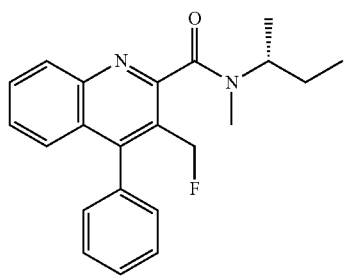

10. The method of claim 6, wherein the compound of formula (I) is a compound of formula (II):

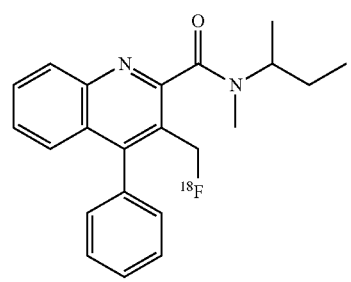

(II)

and salts and solvates thereof.

11. The method of claim 10, wherein the compound of formula (II) is a compound having the structure:

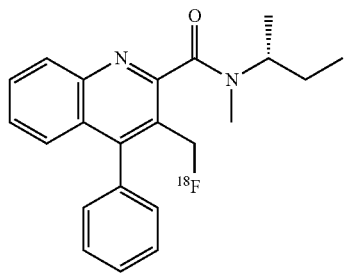

12. The method of claim 7, wherein the subject is a human subject.

13. The compound of claim 1, wherein the compound of formula (I) is prepared from a compound of formula (III), by substitution of the bromine in the compound of formula (III) with fluorine, wherein the compound of formula (III) is:

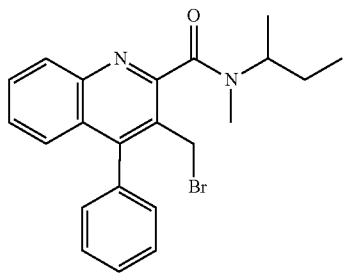

(III)

and salts, solvates and radiolabelled forms thereof.

14. The compound of claim 3, wherein the compound formula (II) is prepared from a compound of formula (IV), by substitution of the chlorine in the compound of formula (IV) with 18-fluorine, wherein the compound of formula (IV) is:

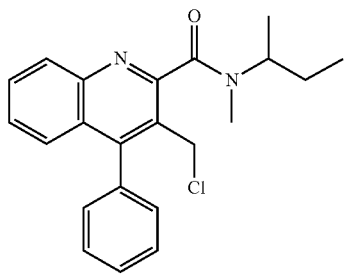

(IV)

and salts, solvates and radiolabelled forms thereof.

15. The complex of claim 5, wherein the stoichiometry of the compound and the TSPO in the complex is 1:1.

16. The method of claim 7, wherein the compound is a radiolabelled compound of formula (I) and the radiolabelled compound of formula (I) is administered to a subject in a fluid composition at a concentration of at least 1 MBq/mL.

* * * * *